(12) United States Patent
Brooks

(10) Patent No.: US 7,794,386 B2
(45) Date of Patent: *Sep. 14, 2010

(54) METHODS FOR FACILITATING WEIGHT LOSS

(75) Inventor: Gregory F. Brooks, Irvine, CA (US)

(73) Assignee: Allergan, Inc., Irvine, CA (US)

( * ) Notice: Subject to any disclaimer, the term of this patent is extended or adjusted under 35 U.S.C. 154(b) by 1145 days.

This patent is subject to a terminal disclaimer.

(21) Appl. No.: 11/376,667

(22) Filed: Mar. 15, 2006

(65) Prior Publication Data

US 2007/0218083 A1    Sep. 20, 2007

(51) Int. Cl.
*A61F 2/00* (2006.01)
(52) U.S. Cl. ................................................ 600/37
(58) Field of Classification Search .............. 600/37, 600/29–32; 128/897–899; 424/183.1, 236.1, 424/239.1, 247.1, 423, 484
See application file for complete search history.

(56) References Cited

U.S. PATENT DOCUMENTS

| | | | |
|---|---|---|---|
| 5,427,291 A | 6/1995 | Smith | 224/250 |
| 5,437,291 A | 8/1995 | Pasricha et al. | 128/898 |
| 5,670,484 A | 9/1997 | Binder | 514/14 |
| 5,674,205 A | 10/1997 | Pasricha et al. | 604/232 |
| 5,714,468 A | 2/1998 | Binder | 514/14 |
| 5,766,605 A | 6/1998 | Sanders et al. | 424/239.1 |
| 5,989,545 A | 11/1999 | Foster et al. | 424/183.1 |
| 6,063,768 A | 5/2000 | First | 514/14 |
| 6,113,915 A | 9/2000 | Aoki et al. | 424/236.1 |
| 6,139,845 A | 10/2000 | Donovan | 424/236.1 |
| 6,143,306 A | 11/2000 | Donovan | 424/236.1 |
| 6,265,379 B1 | 7/2001 | Donovan | 514/14 |
| 6,299,893 B1 | 10/2001 | Schwartz et al. | 424/422 |
| 6,306,403 B1 | 10/2001 | Donovan | 424/239.1 |
| 6,312,708 B1 | 11/2001 | Donovan | 424/423 |
| 6,328,977 B1 | 12/2001 | Donovan | 424/239.1 |
| 6,358,513 B1 | 3/2002 | Voet et al. | 424/239.1 |
| 6,365,164 B1 | 4/2002 | Schmidt | 424/239.1 |
| 6,395,277 B1 | 5/2002 | Graham | 424/184.1 |
| 6,423,319 B1 | 7/2002 | Brooks et al. | 424/239.1 |
| 6,458,365 B1 | 10/2002 | Aoki et al. | 424/239.1 |

(Continued)

FOREIGN PATENT DOCUMENTS

EP    0 605 501 B1    9/1992

(Continued)

OTHER PUBLICATIONS

T Ezri et al. "Anesthesia for restrictive bariatric surgery (gastric bypass not included): laparoscopic vs open procedures." International Journal of Obesity (2004). vol. 28, p. 1157-1162.*

(Continued)

*Primary Examiner*—Charles A Marmor, II
*Assistant Examiner*—Christine D Hopkins
(74) *Attorney, Agent, or Firm*—Claude L. Nassif; Kenton Abel; Debra Condino

(57) ABSTRACT

The present invention provides methods for facilitating weight loss in a patient. In some embodiments, the methods comprise the steps of locally administering a botulinum toxin to a stomach tissue of an obese patient, and deploying a gastric band around the stomach of the patient.

33 Claims, 7 Drawing Sheets

U.S. PATENT DOCUMENTS

| | | | |
|---|---|---|---|
| 6,464,986 B1 | 10/2002 | Aoki et al. | 424/239.1 |
| 6,579,847 B1 | 6/2003 | Unger | 514/2 |
| 6,767,544 B2 | 7/2004 | Brooks et al. | 424/247.1 |
| 2004/0009224 A1 | 1/2004 | Miller | 424/484 |
| 2004/0037865 A1 | 2/2004 | Miller | 424/423 |
| 2004/0086532 A1* | 5/2004 | Donovan | 424/239.1 |
| 2004/0122452 A1 | 6/2004 | Deem et al. | |
| 2004/0253274 A1* | 12/2004 | Voet | 424/239.1 |
| 2005/0175703 A1* | 8/2005 | Hunter et al. | 424/486 |
| 2006/0015151 A1* | 1/2006 | Aldrich | 607/40 |
| 2008/0092910 A1* | 4/2008 | Brooks | 128/898 |

FOREIGN PATENT DOCUMENTS

| | | |
|---|---|---|
| WO | WO 95/17904 | 7/1995 |
| WO | WO 02/13854 A1 | 2/2002 |
| WO | WO 2007/106727 A | 9/2007 |

OTHER PUBLICATIONS

Albanese A. et al., *Review article: the use of botulinum toxin in the alimentary tract*, Ailment Pharmacol Ther 1995; 9, pp. 599-604.

Albanese A., et al., *The use of botulinum toxin on smooth muscles*, Eur J Neurol Nov. 1995; 2(Supp 3), pp. 29-33.

Albani et al., *Safety and efficacy of therapy with botulinum toxin in obesity: a pilot study*, J. Gastroenterol 2005, 40, pp. 833-835.

Bigalke H., et al., *Botulinum A Clostridial toxin Inhibits Non-Cholinergic Synaptic Transmission in Mouse Spinal Cord Neurons in Culture*, Brain Research, 1985, 360, pp. 318-324.

Bigalke H., et al., *Tetanus Toxin and Botulinum A Toxin Inhibit Release and Uptake of Various Transmitters, as Studied with Particulate Preparations From Rat Brain and Spinal Cord*, Naunyn-Schmiedeberg's Arch Pharmacol, 1981, 316, pp. 244-251.

Binz T. et al., *The Complete Sequence of Botulinum Clostridial toxin Type A and Comparison with Other Clostridial toxins*, J Biological Chemistry 265(16), 1990, pp. 9153-9158.

Boyd R.S. et al., *The effect of botulinum Clostridial toxin-B on insulin release from a ∃-cell line*, published at Mov Disord, 10(3):376:1995.

Boyd R.S. et al., *The insulin secreting ∃-cell line, HIT-15, contains SNAP-25 which is a target for botulinum Clostridial toxin-A*, published at Mov Disord, 10(3):376:1995.

Check, *Yet Another Variation on Surgery for Obesity*, Journal of the American Medical Association, Oct. 22/29, 1982, vol. 248, No. 16, pp. 1939, 1943.

Coffield et al., Neurological Disease and Therapy, Eds. Jankovic J. et al., *Therapy With Botulinum Toxin*, Marcel Dekker, Inc., (1994), Chapter 1.

Dykstra, D.D., et al, *Treatment of detrusor-sphincter dyssynergia with botulinum A toxin: A double-blind study*, Arch Phys Med Rehabil Jan. 1990, 71, pp. 24-26.

Eaker, E.Y., et al., *Untoward effects of esophageal botulinum toxin injection in the treatment of achalasia*, Dig Dis Sci Apr. 1997;42(4), p. 724-7.

Garcia-Compean et al., *Endoscopic injection of botulinum toxin in the gastric antrum for the treatment of obesity*, Gastroenterol Clin Biol 2005, 29(8-9), pp. 789-791.

Gonelle-Gispert, C., et al., *SNAP-25a and -25b isoforms are both expressed in insulin-secreting cells and can function in insulin secretion*, Biochem J., 1999, 1, 339 (pt 1), pp. 159-165.

Gui D. et al., *Effects of botulinum toxin on gastric emptying and digestive secretions. A possible tool for correction of obesity?*, Naunyn Schmiedebergs Arch Pharmacol Jun. 2002; 365(Suppl 2), p. R22.

Gui D., et al., *Botulinum toxin injected in the gastric wall reduces body weight and food intake in rats*, Aliment Pharmacol Ther Jun. 2000;14(6), pp. 829-834.

Gui, D., et al., *Effect of botulinum toxin antral injection on gastric emptying and weight reduction in obese patients: a pilot study*, Aliment Pharmacol. Ther., 23, pp. 675-680.

Habermann E., et al., *Tetanus Toxin and Botulinum A and C Clostridial toxins Inhibit Noradrenaline Release From Cultured Mouse Brain*, J Neurochem, 1988 51, 2, pp. 522-527.

Habermann E., *Inhibition by Tetanus and Botulinum A Toxin of the release of [$^3$H]Noradrenaline and [$^3$H]GABA From Rat Brain Homogenate*, Experientia, 1988, 44, pp. 224-226.

Habermann, ($^{125}$I-labelled Clostridial toxin from clostridium botulinum A: preparation, binding to synaptosomes and ascent to the spinal cord, Naunyn-Schmiedeberg's Arch. Pharmacol. 1974; 281, pp. 47-56.

Harrison's Principles of Internal Medicine (1998), edited by Anthony Fauci et al., 14$^{th}$ edition, published by McGraw Hill.

Kohl A., et al., *Comparison of the effect of botulinum toxin A (BOTOX (R)) with the highly-purified Clostridial toxin (NT 201) in the extensor digitorum brevis muscle test*, Mov Disord 2000;15(Suppl 3), p. 165.

Kondo T., et al., *Modification of the action of pentagastrin on acid secretion by botulinum toxin*, Experientia 1977;33, pp. 750-751.

Marjama-Lyons, J., et al., *Tremor-Predominant Parkinson's Disease*, 2000, Drugs & Aging 16(4), pp. 273-278.

Moyer E et al., *Botulinum Toxin Type B: Experimental and Clinical Experience*, "Therapy with Botulinum Toxin", edited by Jankovic, J. et al. (1994), Marcel Dekker, Inc., chapter 6.

Naumann M., et al., *Botulinum toxin type A in the treatment of focal, axillary and palmar hyperhidrosis and other hyperhidrotic conditions*, 1999, European J. Neurology 6 (Supp 4); pp. S111-S115.

Pearce, L.B., *Pharmacologic Characterization of Botulinum Toxin for Basic Science and Medicine*, Toxicon 35(9), pp. 1373-1412.

Porta et al. (Mov Disord 2004, 19(9):S431 ABP1264.

Ragona, R.M., et al., *Management of parotid sialocele with botulinum toxin*, 1999, The Laryngoscope 109, pp. 1344-1346.

Rohrbach S., et al., *Botulinum toxin type A induces apoptosis in nasal glands of guinea pigs*, Ann Otol Rhinol Laryngol Nov. 2001;110(11), pp. 1045-1050.

Rohrbach S., et al., *Minimally invasive application of botulinum toxin type A in nasal hypersecretion*, J Oto-Rhino-Laryngol Nov.-Dec. 2001;63(6), pp. 382-384.

Rolnik J., et al., *Antral Injections of botulinum toxin for the treatment of obesity*, Ann Intern Med Feb. 2003, 18;138(4), pp. 359-360.

Rossi S., et al., *Immunohistochemical localization of SNAP-25 protein in the stomach of rat*, Naunyn Schmiedebergs Arch Pharmacol 2002;365(Suppl 2), p. R37.

Sanchez-Prieto, J., et al., *Botulinum Toxin A Blocks Glutamate Exocytosis From Guinea Pig Cerebral Cortical Synaptosomes*, Eur J. Biochem, 1987, 165, pp. 675-681.

Schantz E.J., et al. Preparation and characterization of botulinum toxin type A for human treatment, eds. Jankovic, J., et al, *Therapy with Botulinum Toxin*, Marcel Dekker, Inc (1994), Chapter 3.

Schantz, E.J., et al, *Properties and use of Botulinum toxin and Other Microbial Clostridial toxins in Medicine*,1992, Microbiol Rev. 56, pp. 80-99.

Singh, *Critical Aspects of Bacterial Protein Toxins*, pp. 63-84 (chapter 4) of Natural Toxins II, edited by B.R. Singh et al., Plenum Press, New York (1996).

Sloop, *Neurology*, 1997, 48, pp. 249-253.

Solhaug, "Gastric Banding: A New Method in the Treatment of Morbid Obesity," Current Surgery, Nov.-Dec. 1983, pp. 424-428.

Wang Z., et al., *Effects of botulinum toxin on gastric myoelectrical and vagal activities in dogs*, Gastroenterology Apr. 2001;120(5 Suppl 1), p. A-718.

Weigand et al, ($^{125}$I-labelled botulinum A Clostridial toxin:pharmacokinetics in cats after intramuscular injection, Nauny-Schmiedeberg's Arch. Pharmacol. 1976; 292, pp. 161-165.

Wiesel P.H. et al., *Botulinum toxin for refractory postoperative pyloric spasm*, Endoscopy 1997;29(2), p. 132.

Durrans D. et al: "Comparison of Weight Loss With Short Term Dietary and Intragastric Balloon Treatment" Gut, British Medical Association, London, vol. 30, No. 5, Jan. 1, 1989, pp. 565-568.

Gui D. et al: "Botulinum Toxin Injected in the Gastric Wall Reduces Body Weight And Food Intake in Rats" Alimentary Pharmacology & Therapeutics, Blackwell Scientific Publications LTD., Cambridge, GB, vol. 14, No. 6, Jun. 1, 2000m pp. 829-834.

U.S. Appl. No. 11/540,177, filed Sep. 29, 2006, Birk.

U.S. Appl. No. 11/582,775, filed Oct. 16, 2006, Brooks.

* cited by examiner

METHODS FOR FACILITATING WEIGHT LOSS

BACKGROUND

The present invention relates to methods for facilitating weight loss. In particular, the present invention relates to methods for reducing weight loss by the use of a gastric band in conjunction with an administration of a neurotoxin, e.g., a botulinum toxin, at or in a vicinity of the gastric band.

Affecting weight loss is one of the key steps in the treatment of obesity. Obesity, especially morbid obesity, is a condition that is associated with a multitude of other hazards to health that include reduced life expectancy and has even been associated with serious sociopsychologic and economic problems.

Gastric Bands

An effective method that has been used to facilitate weight loss includes the deployment of a band around a portion of the stomach creating a stoma opening that is less in diameter than the stomach for restricting food intake into the lower digestive portion of the stomach. The band is commonly called a gastric band. Commercially available gastric bands are sold by Inamed, CA, USA, under the tradename LAP-BAND® System.

Typically, the band is made of a nonextensible material and is located on the outside of the stomach thereby prohibiting the stoma opening to expand. An important feature of the band deployed around the stomach is that it is adjustable. Adjustment is accomplished by means of a balloon that lines the inside of the band. On the day of surgery, when the band is deployed, the balloon is empty and this provides only a slight restriction to eating. Over the weeks and months following surgery the balloon within the band is gradually filled (outlet is tightened) to provide progressively increasing restriction that is matched or "tuned" to each patient.

The balloon adjustment is accomplished using an access port (which is buried under the skin) to increase or decrease the amount of saline fluid contained in the balloon. This banding procedure has been described in articles by Solhaug, "Gastric Banding: A New Method in the Treatment of Morbid Obesity," Current Surgery, pp. 424-428, November-December 1983; and Check, "Yet Another Variation on Surgery for Obesity," Journal of the American Medical Association, Vol. 248, No. 16, pp. 1939, 1943, Oct. 22/29, 1982.

There are several key features that make the band an attractive surgical technique for weight loss: laparoscopic deployment, no division or anastomosis of stomach or bowel, removable and adjustable. The first two of the features above probably reduce the risk of surgery, which is especially important when operating on patients who suffer from morbid obesity. The fact that there is no cutting or repositioning of any intestine brings the risk of leak or obstruction to very low levels (not impossible, as outlined in the risks section below). The fact that the procedure is almost always done laparoscopically may allow decreased stress on the vital organs (heart, lungs, etc.) and may allow quicker recovery in comparison to open procedures.

"Removable" in the list of key features refers to the fact that the band can be removed from the patient with little residual impact on the stomach. This seems to be true even when the band has eroded into the stomach, or become infected, or slipped out of position. This is possible because the silastic substance from which the band is made creates essentially no tissue reaction, so that the band is not stuck in place over time. This feature also means that the band procedure is "reversible" in a certain sense.

The feature of the band that deserves more attention is that it is adjustable. This is the feature that makes the band (in many published reports) successful in helping patients achieve significant sustained weight loss. After all, if the band were not successful, then the decrease in operative risk would not mean much. As long as the patient and surgeon continue to work together, it is usually possible to adjust the band to the patient's needs at that time.

A major advantage in using the band is that it allows for a slower weight loss. The band aims to create slower and steadier weight loss than the results seen after most other surgical procedures. Most weight loss operations create very rapid weight loss in the first few months, which then slows and stabilizes at 10-18 months after surgery. On the other hand, band patients begin with a relatively loose band that allows ongoing intake of nutrition, and the band is gradually "tightened" according to the patient's weight progress and satiety symptoms. This approach aims to achieve a weight loss of 1-2 pounds per week that continues up to or beyond 30 months after surgery.

The use of a gastric band for facilitating weight loss has great promise due to its simplicity and effectiveness. However, the step of deploying the band around the stomach and/or adjusting (i.e., tightening/loosening) the band may be challenging due to the stiffness of the stomach. Further, after the band is deployed around the upper stomach, the band can slip out of its correct position. If it slips out of position, it is likely to cause obstruction of the stomach, requiring urgent re-operation to reposition the band.

The challenges of deploying the gastric band around the stomach and the risk of the band possibly slipping from its correct position may compromise the full potential use of the gastric band as a technique for affecting weight loss.

Stomach

The stomach is an expanded section of the digestive tube between the esophagus and small intestine. The terms used to describe the major regions of the stomach are shown in FIG. 1. The right side of the stomach shown in FIG. 1 is called the greater curvature and that on the left the lesser curvature. The most distal and narrow section of the stomach is termed the pylorus—as food is liquefied in the stomach it passes through the pyloric canal into the small intestine.

The wall of the stomach consists of four coats: serous, muscular, areolar, and mucous, together with vessels and nerves.

The serous coat (*tunica serosa*) is derived from the peritoneum, and covers the entire surface of the organ, excepting along the greater and lesser curvatures at the points of attachment of the greater and lesser omenta; here the two layers of peritoneum leave a small triangular space, along which the nutrient vessels and nerves pass. On the posterior surface of the stomach, close to the cardiac orifice, there is also a small area uncovered by peritoneum, where the organ is in contact with the under surface of the diaphragm.

The muscular coat (*tunica muscularis*) (FIGS. 1B and 1C) is situated immediately beneath the serous covering, with which it is closely connected. It consists of three sets of smooth muscle fibers: longitudinal, circular and oblique.

The longitudinal fibers (*stratum longitudinale*) are the most superficial, and are arranged in two sets. The first set consists of fibers continuous with the longitudinal fibers of the esophagus; they radiate in a stellate manner from the cardiac orifice and are practically all lost before the pyloric portion is reached. The second set commences on the body of the stomach and passes to the right, its fibers becoming more thickly distributed as they approach the pylorus. Some of the more superficial fibers of this set pass on to the duodenum, but the deeper fibers dip inward and interlace with the circular fibers of the pyloric valve.

The circular fibers (*stratum circulare*) form a uniform layer over the whole extent of the stomach beneath the longitudinal fibers. At the pylorus they are most abundant, and are aggregated into a circular ring, which projects into the lumen, and forms, with the fold of mucous membrane covering its surface, the pyloric valve. They are continuous with the circular fibers of the esophagus, but are sharply marked off from the circular fibers of the duodenum.

The oblique fibers (*fibræobliquæ*) internal to the circular layer, are limited chiefly to the cardiac end of the stomach, where they are disposed as a thick uniform layer, covering both surfaces, some passing obliquely from left to right, others from right to left, around the cardiac end.

The areolar or submucous coat (*tela submucosa*) consists of a loose, areolar tissue, connecting the mucous and muscular layers.

The mucous membrane (*tunica mucosa*) is thick and its surface is smooth, soft, and velvety. In the fresh state it is of a pinkish tinge at the pyloric end, and of a red or reddish-brown color over the rest of its surface. In infancy it is of a brighter hue, the vascular redness being more marked. It is thin at the cardiac extremity, but thicker toward the pylorus. During the contracted state of the organ it is thrown into numerous plaits or rugæ, which, for the most part, have a longitudinal direction, and are most marked toward the pyloric end of the stomach, and along the greater curvature. These folds are entirely obliterated when the organ becomes distended.

Botulinum Toxin

The genus *Clostridium* has more than one hundred and twenty seven species, grouped according to their morphology and functions. The anaerobic, gram positive bacterium *Clostridium botulinum* produces a potent polypeptide Clostridial toxin, botulinum toxin, which causes a neuroparalytic illness in humans and animals referred to as botulism. The spores of *Clostridium botulinum* are found in soil and can grow in improperly sterilized and sealed food containers of home based canneries, which are the cause of many of the cases of botulism. The effects of botulism typically appear 18 to 36 hours after eating the foodstuffs infected with a *Clostridium botulinum* culture or spores. The botulinum toxin can apparently pass unattenuated through the lining of the gut and attack peripheral motor neurons. Symptoms of botulinum toxin intoxication can progress from difficulty walking, swallowing, and speaking to paralysis of the respiratory muscles and death.

Botulinum toxin type A is the most lethal natural biological agent known to man. About 50 picograms of a commercially available botulinum toxin type A (purified Clostridial toxin complex)[1] is a $LD_{50}$ in mice (i.e. 1 unit). One unit of BOTOX® contains about 50 picograms (about 56 attomoles) of botulinum toxin type A complex. Interestingly, on a molar basis, botulinum toxin type A is about 1.8 billion times more lethal than diphtheria, about 600 million times more lethal than sodium cyanide, about 30 million times more lethal than cobra toxin and about 12 million times more lethal than cholera. Singh, *Critical Aspects of Bacterial Protein Toxins*, pages 63-84 (chapter 4) of Natural Toxins II, edited by B. R. Singh et al., Plenum Press, New York (1996) (where the stated $LD_{50}$ of botulinum toxin type A of 0.3 ng equals 1 U is corrected for the fact that about 0.05 ng of BOTOX® equals 1 unit). One unit (U) of botulinum toxin is defined as the $LD_{50}$ upon intraperitoneal injection into female Swiss Webster mice weighing 18 to 20 grams each.

Seven immunologically distinct botulinum Clostridial toxins have been characterized, these being respectively botulinum Clostridial toxin serotypes A, B, $C_1$, D, E, F and G each of which is distinguished by neutralization with type-specific antibodies. The different serotypes of botulinum toxin vary in the animal species that they affect and in the severity and duration of the paralysis they evoke. For example, it has been determined that botulinum toxin type A is 500 times more potent, as measured by the rate of paralysis produced in the rat, than is botulinum toxin type B. Additionally, botulinum toxin type B has been determined to be non-toxic in primates at a dose of 480 U/kg which is about 12 times the primate $LD_{50}$ for botulinum toxin type A. Moyer E et al., *Botulinum Toxin Type B: Experimental and Clinical Experience*, being chapter 6, pages 71-85 of "Therapy with Botulinum Toxin", edited by Jankovic, J. et al. (1994), Marcel Dekker, Inc. Botulinum toxin apparently binds with high affinity to cholinergic motor neurons, is translocated into the neuron and blocks the release of acetylcholine.

Regardless of serotype, the molecular mechanism of toxin intoxication appears to be similar and to involve at least three steps or stages. In the first step of the process, the toxin binds to the presynaptic membrane of the target neuron through a specific interaction between the heavy chain, H chain, and a cell surface receptor; the receptor is thought to be different for each type of botulinum toxin and for tetanus toxin. The carboxyl end segment of the H chain, $H_C$, appears to be important for targeting of the toxin to the cell surface.

In the second step, the toxin crosses the plasma membrane of the poisoned cell. The toxin is first engulfed by the cell through receptor-mediated endocytosis, and an endosome containing the toxin is formed. The toxin then escapes the endosome into the cytoplasm of the cell. This step is thought to be mediated by the amino end segment of the H chain, $H_N$, which triggers a conformational change of the toxin in response to a pH of about 5.5 or lower. Endosomes are known to possess a proton pump which decreases intra-endosomal pH. The conformational shift exposes hydrophobic residues in the toxin, which permits the toxin to embed itself in the endosomal membrane. The toxin (or at a minimum the light chain) then translocates through the endosomal membrane into the cytoplasm.

The last step of the mechanism of botulinum toxin activity appears to involve reduction of the disulfide bond joining the heavy chain, H chain, and the light chain, L chain. The entire toxic activity of botulinum and tetanus toxins is contained in the L chain of the holotoxin; the L chain is a zinc (Zn++) endopeptidase which selectively cleaves proteins essential for recognition and docking of neurotransmitter-containing vesicles with the cytoplasmic surface of the plasma membrane, and fusion of the vesicles with the plasma membrane. Tetanus Clostridial toxin, botulinum toxin types B, D, F, and G cause degradation of synaptobrevin (also called vesicle-associated membrane protein (VAMP)), a synaptosomal membrane protein. Most of the VAMP present at the cytoplasmic surface of the synaptic vesicle is removed as a result of any one of these cleavage events. Botulinum toxin serotype A and E cleave SNAP-25. Botulinum toxin serotype $C_1$ was originally thought to cleave syntaxin, but was found to cleave syntaxin and SNAP-25. Each of the botulinum toxins specifically cleaves a different bond, except botulinum toxin type B (and tetanus toxin) which cleave the same bond.

Although all the botulinum toxins serotypes apparently inhibit release of the neurotransmitter acetylcholine at the neuromuscular junction, they do so by affecting different neurosecretory proteins and/or cleaving these proteins at different sites. For example, botulinum types A and E both cleave the 25 kiloDalton (kD) synaptosomal associated protein (SNAP-25), but they target different amino acid sequences within this protein. Botulinum toxin types B, D, F and G act on vesicle-associated protein (VAMP, also called synaptobrevin), with each serotype cleaving the protein at a different site. Finally, botulinum toxin type $C_1$ has been shown to cleave both syntaxin and SNAP-25. These differences in mechanism of action may affect the relative potency and/or duration of action of the various botulinum toxin serotypes. Apparently, a substrate for a botulinum toxin can be found in a variety of different cell types. See e.g. Gonelle-Gispert, C., et al., *SNAP-25a and -25b isoforms are both expressed in insulin-secreting cells and can function in insulin secretion*, Biochem J. 1; 339 (pt 1):159-65:1999, and Boyd R. S. et al., *The effect of botulinum Clostridial toxin-B on insulin release from a ∃-cell line*, and Boyd R. S. et al., *The insulin secreting ∃-cell line, HIT-15, contains SNAP-25 which is a target for botulinum Clostridial toxin-A*, both published at *Mov Disord*, 10(3):376:1995 (pancreatic islet B cells contains at least SNAP-25 and synaptobrevin).

The molecular weight of the botulinum toxin protein molecule, for all seven of the known botulinum toxin serotypes, is about 150 kD. Interestingly, the botulinum toxins are released by Clostridial bacterium as complexes comprising the 150 kD botulinum toxin protein molecule along with associated non-toxin proteins. Thus, the botulinum toxin type A complex can be produced by Clostridial bacterium as 900 kD, 500 kD and 300 kD forms. Botulinum toxin types B and $C_1$ are apparently produced as only a 700 kD or 500 kD complex. Botulinum toxin type D is produced as both 300 kD and 500 kD complexes. Finally, botulinum toxin types E and F are produced as only approximately 300 kD complexes. The complexes (i.e. molecular weight greater than about 150 kD) are believed to contain a non-toxin hemaglutinin protein and a non-toxin and non-toxic nonhemaglutinin protein. These two non-toxin proteins (which along with the botulinum toxin molecule comprise the relevant Clostridial toxin complex) may act to provide stability against denaturation to the botulinum toxin molecule and protection against digestive acids when toxin is ingested. Additionally, it is possible that the larger (greater than about 150 kD molecular weight) botulinum toxin complexes may result in a slower rate of diffusion of the botulinum toxin away from a site of intramuscular injection of a botulinum toxin complex.

All the botulinum toxin serotypes are made by *Clostridium botulinum* bacteria as inactive single chain proteins which must be cleaved or nicked by proteases to become neuroactive. The bacterial strains that make botulinum toxin serotypes A and G possess endogenous proteases and serotypes A and G can therefore be recovered from bacterial cultures in predominantly their active form. In contrast, botulinum toxin serotypes $C_1$, D, and E are synthesized by nonproteolytic strains and are therefore typically unactivated when recovered from culture. Serotypes B and F are produced by both proteolytic and nonproteolytic strains and therefore can be recovered in either the active or inactive form. However, even the proteolytic strains that produce, for example, the botulinum toxin type B serotype only cleave a portion of the toxin produced. The exact proportion of nicked to unnicked molecules depends on the length of incubation and the temperature of the culture. Therefore, a certain percentage of any preparation of, for example, the botulinum toxin type B toxin is likely to be inactive, possibly accounting for a lower potency of botulinum toxin type B as compared to botulinum toxin type A. The presence of inactive botulinum toxin molecules in a clinical preparation will contribute to the overall protein load of the preparation, which has been linked to increased antigenicity, without contributing to its clinical efficacy.

Botulinum toxins and toxin complexes can be obtained from, for example, List Biological Laboratories, Inc., Campbell, Calif.; the Centre for Applied Microbiology and Research, Porton Down, U.K.; Wako (Osaka, Japan), as well as from Sigma Chemicals of St Louis, Mo. Commercially available botulinum toxin containing pharmaceutical compositions include BOTOX® (Botulinum toxin type A Clostridial toxin complex with human serum albumin and sodium chloride) available from Allergan, Inc., of Irvine, Calif. in 100 unit vials as a lyophilized powder to be reconstituted with 0.9% sodium chloride before use), Dysport® (Clostridium botulinum type A toxin haemagglutinin complex with human serum albumin and lactose in the formulation), available from Ipsen Limited, Berkshire, U.K. as a powder to be reconstituted with 0.9% sodium chloride before use), and MyoBloc™ (an injectable solution comprising botulinum toxin type B, human serum albumin, sodium succinate, and sodium chloride at about pH 5.6, available from Elan Corporation, Dublin, Ireland).

The success of botulinum toxin type A to treat a variety of clinical conditions has led to interest in other botulinum toxin serotypes. Additionally, pure botulinum toxin has been used to treat humans. See e.g. Kohl A., et al., *Comparison of the effect of botulinum toxin A (BOTOX (R)) with the highly-purified Clostridial toxin (NT 201) in the extensor digitorum brevis muscle test*, Mov Disord 2000; 15(Suppl 3):165. Hence, a pharmaceutical composition can be prepared using a pure botulinum toxin.

The type A botulinum toxin is known to be soluble in dilute aqueous solutions at pH 4-6.8. At pH above about 7 the stabilizing nontoxic proteins dissociate from the Clostridial toxin, resulting in a gradual loss of toxicity, particularly as the pH and temperature rise. Schantz E. J., et al *Preparation and characterization of botulinum toxin type A for human treatment* (in particular pages 44-45), being chapter 3 of Jankovic, J., et al, *Therapy with Botulinum Toxin*, Marcel Dekker, Inc (1994).

The botulinum toxin molecule (about 150 kDa), as well as the botulinum toxin complexes (about 300-900 kDa), such as the toxin type A complex are also extremely susceptible to denaturation due to surface denaturation, heat, and alkaline conditions. Inactivated toxin forms toxoid proteins which may be immunogenic. The resulting antibodies can render a patient refractory to toxin injection.

In vitro studies have indicated that botulinum toxin inhibits potassium cation induced release of both acetylcholine and norepinephrine from primary cell cultures of brainstem tissue. Additionally, it has been reported that botulinum toxin inhibits the evoked release of both glycine and glutamate in primary cultures of spinal cord neurons and that in brain synaptosome preparations botulinum toxin inhibits the release of each of the neurotransmitters acetylcholine, dopamine, norepinephrine (Habermann E., et al., *Tetanus Toxin and Botulinum A and C Clostridial toxins Inhibit Noradrenaline Release From Cultured Mouse Brain*, J Neurochem 51(2);522-527:1988) CGRP, substance P and glutamate (Sanchez-Prieto, J., et al., *Botulinum Toxin A Blocks Glutamate Exocytosis From Guinea Pig Cerebral Cortical Synaptosomes*, Eur J. Biochem 165; 675-681:1987. Thus, when adequate concentrations are used, stimulus-evoked release of most neurotransmitters is blocked by botulinum toxin. See e.g. Pearce, L. B., *Pharmacologic Characterization of Botulinum Toxin For Basic Science and Medicine*, Toxicon 35(9); 1373-1412 at 1393; Bigalke H., et al., *Botu-*

*linum A Clostridial toxin Inhibits Non-Cholinergic Synaptic Transmission in Mouse Spinal Cord Neurons in Culture*, Brain Research 360; 318-324:1985; Habermann E., *Inhibition by Tetanus and Botulinum A Toxin of the release of [³H]Noradrenaline and [³H]GABA From Rat Brain Homogenate*, Experientia 44; 224-226:1988, Bigalke H., et al., *Tetanus Toxin and Botulinum A Toxin Inhibit Release and Uptake of Various Transmitters, as Studied with Particulate Preparations From Rat Brain and Spinal Cord*, Naunyn-Schmiedeberg's Arch Pharmacol 316; 244-251:1981, and; Jankovic J. et al., *Therapy With Botulinum Toxin*, Marcel Dekker, Inc., (1994), page 5.

Botulinum toxin type A can be obtained by establishing and growing cultures of *Clostridium botulinum* in a fermenter and then harvesting and purifying the fermented mixture in accordance with known procedures. All the botulinum toxin serotypes are initially synthesized as inactive single chain proteins which must be cleaved or nicked by proteases to become neuroactive. The bacterial strains that make botulinum toxin serotypes A and G possess endogenous proteases and serotypes A and G can therefore be recovered from bacterial cultures in predominantly their active form. In contrast, botulinum toxin serotypes $C_1$, D and E are synthesized by nonproteolytic strains and are therefore typically unactivated when recovered from culture. Serotypes B and F are produced by both proteolytic and nonproteolytic strains and therefore can be recovered in either the active or inactive form. However, even the proteolytic strains that produce, for example, the botulinum toxin type B serotype only cleave a portion of the toxin produced. The exact proportion of nicked to unnicked molecules depends on the length of incubation and the temperature of the culture. Therefore, a certain percentage of any preparation of, for example, the botulinum toxin type B toxin is likely to be inactive, possibly accounting for the known significantly lower potency of botulinum toxin type B as compared to botulinum toxin type A. The presence of inactive botulinum toxin molecules in a clinical preparation will contribute to the overall protein load of the preparation, which has been linked to increased antigenicity, without contributing to its clinical efficacy. Additionally, it is known that botulinum toxin type B has, upon intramuscular injection, a shorter duration of activity and is also less potent than botulinum toxin type A at the same dose level.

High quality crystalline botulinum toxin type A can be produced from the Hall A strain of *Clostridium botulinum* with characteristics of $\geq 3 \times 10^7$ U/mg, an $A_{260}/A_{278}$ of less than 0.60 and a distinct pattern of banding on gel electrophoresis. The known Schantz process can be used to obtain crystalline botulinum toxin type A, as set forth in Schantz, E. J., et al, *Properties and use of Botulinum toxin and Other Microbial Clostridial toxins in Medicine*, Microbiol Rev. 56; 80-99:1992. Generally, the botulinum toxin type A complex can be isolated and purified from an anaerobic fermentation by cultivating *Clostridium botulinum* type A in a suitable medium. The known process can also be used, upon separation out of the non-toxin proteins, to obtain pure botulinum toxins, such as for example: purified botulinum toxin type A with an approximately 150 kD molecular weight with a specific potency of $1-2 \times 10^8$ $LD_{50}$ U/mg or greater; purified botulinum toxin type B with an approximately 156 kD molecular weight with a specific potency of $1-2 \times 10^8$ $LD_{50}$ U/mg or greater, and; purified botulinum toxin type F with an approximately 155 kD molecular weight with a specific potency of $1-2 \times 10^7$ $LD_{50}$ U/mg or greater.

Either the pure botulinum toxin (i.e. the 150 kilodalton botulinum toxin molecule) or the toxin complex can be used to prepare a pharmaceutical composition. Both molecule and complex are susceptible to denaturation due to surface denaturation, heat, and alkaline conditions. Inactivated toxin forms toxoid proteins which may be immunogenic. The resulting antibodies can render a patient refractory to toxin injection.

As with enzymes generally, the biological activities of the botulinum toxins (which are intracellular peptidases) is dependant, at least in part, upon their three dimensional conformation. Thus, botulinum toxin type A is detoxified by heat, various chemicals surface stretching and surface drying. Additionally, it is known that dilution of the toxin complex obtained by the known culturing, fermentation and purification to the much, much lower toxin concentrations used for pharmaceutical composition formulation results in rapid detoxification of the toxin unless a suitable stabilizing agent is present. Dilution of the toxin from milligram quantities to a solution containing nanograms per milliliter presents significant difficulties because of the rapid loss of specific toxicity upon such great dilution. Since the toxin may be used months or years after the toxin containing pharmaceutical composition is formulated, the toxin can stabilized with a stabilizing agent such as albumin and gelatin.

A commercially available botulinum toxin containing pharmaceutical composition is sold under the trademark BOTOX® (available from Allergan, Inc., of Irvine, Calif.). BOTOX® consists of a purified botulinum toxin type A complex, albumin and sodium chloride packaged in sterile, vacuum-dried form. The botulinum toxin type A is made from a culture of the Hall strain of *Clostridium botulinum* grown in a medium containing N-Z amine and yeast extract. The botulinum toxin type A complex is purified from the culture solution by a series of acid precipitations to a crystalline complex consisting of the active high molecular weight toxin protein and an associated hemagglutinin protein. The crystalline complex is re-dissolved in a solution containing saline and albumin and sterile filtered (0.2 microns) prior to vacuum-drying. The vacuum-dried product is stored in a freezer at or below $-5°$ C. BOTOX® can be reconstituted with sterile, non-preserved saline prior to intramuscular injection. Each vial of BOTOX® contains about 100 units (U) of *Clostridium botulinum* toxin type A purified Clostridial toxin complex, 0.5 milligrams of human serum albumin and 0.9 milligrams of sodium chloride in a sterile, vacuum-dried form without a preservative.

To reconstitute vacuum-dried BOTOX®, sterile normal saline without a preservative; (0.9% Sodium Chloride Injection) is used by drawing up the proper amount of diluent in the appropriate size syringe. Since BOTOX® may be denatured by bubbling or similar violent agitation, the diluent is gently injected into the vial. For sterility reasons BOTOX® is preferably administered within four hours after the vial is removed from the freezer and reconstituted. During these four hours, reconstituted BOTOX® can be stored in a refrigerator at about $2°$ C. to about $8°$ C. Reconstituted, refrigerated BOTOX® has been reported to retain its potency for at least about two weeks. *Neurology*, 48:249-53:1997.

Botulinum toxins have been used in clinical settings for the treatment of neuromuscular disorders characterized by hyperactive skeletal muscles. Botulinum toxin type A (BOTOX®) was approved by the U.S. Food and Drug Administration in 1989 for the treatment of essential blepharospasm, strabismus and hemifacial spasm in patients over the age of twelve. In 2000 the FDA approved commercial preparations of type A (BOTOX®) and type B botulinum toxin (MyoBloc™) serotypes for the treatment of cervical dystonia, and in 2002 the FDA approved a type A botulinum toxin (BOTOX®) for the cosmetic treatment of certain hyperkinetic (glabellar)

facial wrinkles. Clinical effects of peripheral intramuscular botulinum toxin type A are usually seen within one week of injection and sometimes within a few hours. The typical duration of symptomatic relief (i.e. flaccid muscle paralysis) from a single intramuscular injection of botulinum toxin type A can be about three months, although in some cases the effects of a botulinum toxin induced denervation of a gland, such as a salivary gland, have been reported to last for several years. For example, it is known that botulinum toxin type A can have an efficacy for up to 12 months (Naumann M., et al., *Botulinum toxin type A in the treatment of focal, axillary and palmar hyperhidrosis and other hyperhidrotic conditions*, European J. Neurology 6 (Supp 4): S111-S115:1999), and in some circumstances for as long as 27 months. Ragona, R. M., et al., *Management of parotid sialocele with botulinum toxin*, The Laryngoscope 109:1344-1346:1999. However, the usual duration of an intramuscular injection of BOTOX® is typically about 3 to 4 months.

It has been reported that a botulinum toxin type A has been used in diverse clinical settings, including for example as follows:

(1) about 75-125 units of BOTOX® per intramuscular injection (multiple muscles) to treat cervical dystonia;

(2) 5-10 units of BOTOX® per intramuscular injection to treat glabellar lines (brow furrows) (5 units injected intramuscularly into the procerus muscle and 10 units injected intramuscularly into each corrugator supercilii muscle);

(3) about 30-80 units of BOTOX® to treat constipation by intrasphincter injection of the puborectalis muscle;

(4) about 1-5 units per muscle of intramuscularly injected BOTOX® to treat blepharospasm by injecting the lateral pre-tarsal orbicularis oculi muscle of the upper lid and the lateral pre-tarsal orbicularis oculi of the lower lid.

(5) to treat strabismus, extraocular muscles have been injected intramuscularly with between about 1-5 units of BOTOX®, the amount injected varying based upon both the size of the muscle to be injected and the extent of muscle paralysis desired (i.e. amount of diopter correction desired).

(6) to treat upper limb spasticity following stroke by intramuscular injections of BOTOX® into five different upper limb flexor muscles, as follows:

(a) flexor digitorum profundus: 7.5 U to 30 U
(b) flexor digitorum sublimus: 7.5 U to 30 U
(c) flexor carpi ulnaris: 10 U to 40 U
(d) flexor carpi radialis: 15 U to 60 U
(e) biceps brachii: 50 U to 200 U. Each of the five indicated muscles has been injected at the same treatment session, so that the patient receives from 90 U to 360 U of upper limb flexor muscle BOTOX® by intramuscular injection at each treatment session.

(7) to treat migraine, pericranial injected (injected symmetrically into glabellar, frontalis and temporalis muscles) injection of 25 U of BOTOX® has showed significant benefit as a prophylactic treatment of migraine compared to vehicle as measured by decreased measures of migraine frequency, maximal severity, associated vomiting and acute medication use over the three month period following the 25 U injection.

Additionally, intramuscular botulinum toxin has been used in the treatment of tremor in patients with Parkinson's disease, although it has been reported that results have not been impressive. Marjama-Lyons, J., et al., *Tremor-Predominant Parkinson's Disease*, Drugs & Aging 16(4);273-278:2000.

Treatment of certain gastrointestinal and smooth muscle disorders with a botulinum toxin are known. See e.g. U.S. Pat. Nos. 5,427,291 and 5,674,205 (Pasricha). Additionally, transurethral injection of a botulinum toxin into a bladder sphincter to treat a urination disorder is known (see e.g. Dykstra, D. D., et al, *Treatment of detrusor-sphincter dyssynergia with botulinum A toxin: A double-blind study*, Arch Phys Med Rehabil 1990 January; 71:24-6), as is injection of a botulinum toxin into the prostate to treat prostatic hyperplasia. See e.g. U.S. Pat. No. 6,365,164 (Schmidt).

U.S. Pat. No. 5,766,605 (Sanders) proposes the treatment of various autonomic disorders, such as excessive stomach acid secretion, hypersalivation, rhinittis, with a botulinum toxin. Additionally, It is known that nasal hypersecretion is predominantly caused by over activity of nasal glands, which are mainly under cholinergic control and it has been demonstrated that application of botulinum toxin type A to mammalian nasal mucosal tissue of the maxillary sinus turbinates can induce a temporary apoptosis in the nasal glands. Rohrbach S., et al., *Botulinum toxin type A induces apoptosis in nasal glands of guinea pigs*, Ann Otol Rhinol Laryngol 2001 November; 110(11):1045-50. Furthermore, local application of botulinum toxin A to a human female patient with intrinsic rhinitis resulted in a clear decrease of the nasal hypersecretion within five days. Rohrbach S., et al., *Minimally invasive application of botulinum toxin type A in nasal hypersecretion*, J Oto-Rhino-Laryngol 2001 November-December; 63(6):382-4.

Various afflictions, such as hyperhydrosis and headache, treatable with a botulinum toxin are discussed in WO 95/17904 (PCT/US94/14717) (Aoki). EP 0 605 501 B1 (Graham) discusses treatment of cerebral palsy with a botulinum toxin and U.S. Pat. No. 6,063,768 (First) discusses treatment of neurogenic inflammation with a botulinum toxin.

In addition to having pharmacologic actions at the peripheral location, botulinum toxins can also have inhibitory effects in the central nervous system. Work by Weigand et al, ($^{125}$*I-labelled botulinum A Clostridial toxin:pharmacokinetics in cats after intramuscular injection*, Nauny-Schmiedeberg's Arch. Pharmacol. 1976; 292, 161-165), and Habermann, ($^{125}$*I-labelled Clostridial toxin from clostridium botulinum A: preparation, binding to synaptosomes and ascent to the spinal cord*, Nauny-Schmiedeberg's Arch. Pharmacol. 1974; 281, 47-56) showed that botulinum toxin is able to ascend to the spinal area by retrograde transport. As such, a botulinum toxin injected at a peripheral location, for example intramuscularly, may be retrograde transported to the spinal cord.

In vitro studies have indicated that botulinum toxin inhibits potassium cation induced release of both acetylcholine and norepinephrine from primary cell cultures of brainstem tissue. Additionally, it has been reported that botulinum toxin inhibits the evoked release of both glycine and glutamate in primary cultures of spinal cord neurons and that in brain synaptosome preparations botulinum toxin inhibits the release of each of the neurotransmitters acetylcholine, dopamine, norepinephrine, CGRP and glutamate.

U.S. Pat. No. 5,989,545 discloses that a modified Clostridial toxin or fragment thereof, preferably a botulinum toxin, chemically conjugated or recombinantly fused to a particular targeting moiety can be used to treat pain by administration of the agent to the spinal cord.

A botulinum toxin has also been proposed for the treatment of hyperhydrosis (excessive sweating, U.S. Pat. No. 5,766, 605), headache, (U.S. Pat. No. 6,458,365), migraine headache (U.S. Pat. No. 5,714,468), post-operative pain and visceral pain (U.S. Pat. No. 6,464,986), pain by intraspinal administration (U.S. Pat. No. 6,113,915), Parkinson's disease by intracranial administration (U.S. Pat. No. 6,306,403), hair growth and hair retention (U.S. Pat. No. 6,299,893), psoriasis and dermatitis (U.S. Pat. No. 5,670,484), injured muscles (U.S. Pat. No. 6,423,319, various cancers (U.S. Pat. No.

6,139,845), pancreatic disorders (U.S. Pat. No. 6,143,306), smooth muscle disorders (U.S. Pat. No. 5,437,291, including injection of a botulinum toxin into the upper and lower esophageal, pyloric and anal sphincters), prostate disorders (U.S. Pat. No. 6,365,164), inflammation, arthritis and gout (U.S. Pat. No. 6,063,768), juvenile cerebral palsy (U.S. Pat. No. 6,395,277), inner ear disorders (U.S. Pat. No. 6,265,379), thyroid disorders (U.S. Pat. No. 6,358,513), parathyroid disorders (U.S. Pat. No. 6,328,977). Additionally, controlled release toxin implants are known (U.S. Pat. Nos. 6,306,423 and 6,312,708).

It has been reported that that intravenous injection of a botulinum toxin causes a decline of pentagastrin stimulated acid and pepsin secretion in rats. Kondo T., et al., *Modification of the action of pentagastrin on acid secretion by botulinum toxin*, Experientia 1977; 33:750-1. Additionally it has been speculated that a botulinum toxin can be used to reduce a gastrointestinal secretion, such as a gastric secretion. See pages 16-17 of WO 95/17904. Furthermore, a botulinum toxin has been proposed for the treatment of disorders of gastrointestinal muscle in the enteric nervous system disorder (U.S. Pat. No. 5,437,291) and well as to treat various autonomic disorders (U.S. Pat. No. 5,766,605). Botulinum toxin has been injected into the fundus of the stomach of dogs. Wang Z., et al., *Effects of botulinum toxin on gastric myoelectrical and vagal activities in dogs*, Gastroenterology 2001 April; 120(5 Suppl 1):A-718. Additionally, intramuscular injection of a botulinum toxin into the gastric antrum has been proposed as a treatment for obesity. See e.g. Gui D., et al., *Effects of botulinum toxin on gastric emptying and digestive secretions. A possible tool for correction of obesity?*, Naunyn Schmiedebergs Arch Pharmacol 2002 June; 365(Suppl 2):R22; Albanese A., et al., *The use of botulinum toxin on smooth muscles*, Eur J Neurol 1995 November; 2(Supp 3):29-33, and; Gui D., et al., *Botulinum toxin injected in the gastric wall reduces body weight and food intake in rats*, Aliment Pharmacol Ther 2000 June; 14(6):829-834. Furthermore, botulinum toxin type A has been proposed as a therapeutic application for the control of secretion in the stomach. Rossi S., et al., *Immunohistochemical localization of SNAP-25 protein in the stomach of rat*, Naunyn Schmiedebergs Arch Pharmacol 2002; 365(Suppl 2):R37.

Significantly, it has been reported that injection of a botulinum toxin into the lower esophageal sphincter for the treatment of achalasia results in the formation of ulcers in the esophagus. Eaker, E.Y., et al., *Untoward effects of esophageal botulinum toxin injection in the treatment of achalasia*, Dig Dis Sci 1997 April; 42(4):724-7. It is know to inject a botulinum toxin into a spastic pyloric sphincter of a patient with a prepyloric ulcer in order to permit the pyloric muscle to open. Wiesel P. H. et al., *Botulinum toxin for refractory postoperative pyloric spasm*, Endoscopy 1997; 29(2): 132.

It is known to inject a botulinum toxin into the stomach wall of a patient to treat obesity by reducing stomach muscle contractions (see e.g. Rolnik J., et al., *Antral Injections of botulinum toxin for the treatment of obesity*, Ann Intern Med 2003 February, 18; 138(4):359-360; 2003, Miller L., WO 02/13854 A1, *Obesity controlling method*, published Feb. 21, 2002; Gui, D. et al., *Botulinum toxin injected in the gastric wall reduces body weight and food intake in rats*, Aliment Pharmacol Ther 2000 June; 14(6):829-834; Gui D. et al., *Effects of botulinum toxin on gastric emptying and digestive secretions. A possible tool for correction of obesity?*, Naunyn Schmiedebergs Arch Pharmacol 2002 June; 365(Suppl 2): R22; Albanese A., et al., *The use of botulinum toxin on smooth muscles*, Eur J Neurol 1995 November; 2 (Supp 3): 29-33; Albanese A. et al., *Review article: the use of botulinum toxin in the alimentary tract*, Ailment Pharmacol Ther 1995; 9: 599-604.

Tetanus toxin, as wells as derivatives (i.e. with a non-native targeting moiety), fragments, hybrids and chimeras thereof can also have therapeutic utility. The tetanus toxin bears many similarities to the botulinum toxins. Thus, both the tetanus toxin and the botulinum toxins are polypeptides made by closely related species of *Clostridium* (*Clostridium tetani* and *Clostridium botulinum*, respectively). Additionally, both the tetanus toxin and the botulinum toxins are dichain proteins composed of a light chain (molecular weight about 50 kD) covalently bound by a single disulfide bond to a heavy chain (molecular weight about 100 kD). Hence, the molecular weight of tetanus toxin and of each of the seven botulinum toxins (non-complexed) is about 150 kD. Furthermore, for both the tetanus toxin and the botulinum toxins, the light chain bears the domain which exhibits intracellular biological (protease) activity, while the heavy chain comprises the receptor binding (immunogenic) and cell membrane translocational domains.

Further, both the tetanus toxin and the botulinum toxins exhibit a high, specific affinity for gangliocide receptors on the surface of presynaptic cholinergic neurons. Receptor mediated endocytosis of tetanus toxin by peripheral cholinergic neurons results in retrograde axonal transport, blocking of the release of inhibitory neurotransmitters from central synapses and a spastic paralysis. Contrarily, receptor mediated endocytosis of botulinum toxin by peripheral cholinergic neurons results in little if any retrograde transport, inhibition of acetylcholine exocytosis from the intoxicated peripheral motor neurons and a flaccid paralysis.

Finally, the tetanus toxin and the botulinum toxins resemble each other in both biosynthesis and molecular architecture. Thus, there is an overall 34% identity between the protein sequences of tetanus toxin and botulinum toxin type A, and a sequence identity as high as 62% for some functional domains. Binz T. et al., *The Complete Sequence of Botulinum Clostridial toxin Type A and Comparison with Other Clostridial toxins*, J Biological Chemistry 265(16);9153-9158:1990.

Acetylcholine

Typically only a single type of small molecule neurotransmitter is released by each type of neuron in the mammalian nervous system. The neurotransmitter acetylcholine is secreted by neurons in many areas of the brain, but specifically by the large pyramidal cells of the motor cortex, by several different neurons in the basal ganglia, by the motor neurons that innervate the skeletal muscles, by the preganglionic neurons of the autonomic nervous system (both sympathetic and parasympathetic), by the postganglionic neurons of the parasympathetic nervous system, and by some of the postganglionic neurons of the sympathetic nervous system. Essentially, only the postganglionic sympathetic nerve fibers to the sweat glands, the piloerector muscles and a few blood vessels are cholinergic as most of the postganglionic neurons of the sympathetic nervous system secret the neurotransmitter norepinephrine. In most instances acetylcholine has an excitatory effect. However, acetylcholine is known to have inhibitory effects at some of the peripheral parasympathetic nerve endings, such as inhibition of heart rate by the vagal nerve.

The efferent signals of the autonomic nervous system are transmitted to the body through either the sympathetic nervous system or the parasympathetic nervous system. The preganglionic neurons of the sympathetic nervous system extend from preganglionic sympathetic neuron cell bodies located in the intermediolateral horn of the spinal cord. The preganglionic sympathetic nerve fibers, extending from the cell body, synapse with postganglionic neurons located in either a paravertebral sympathetic ganglion or in a prevertebral ganglion. Since the preganglionic neurons of both the sympathetic and parasympathetic nervous system are cholinergic, application of acetylcholine to the ganglia will excite both sympathetic and parasympathetic postganglionic neurons.

Acetylcholine activates two types of receptors, muscarinic and nicotinic receptors. The muscarinic receptors are found in all effector cells stimulated by the postganglionic, neurons of the parasympathetic nervous system as well as in those stimulated by the postganglionic cholinergic neurons of the sympathetic nervous system. The nicotinic receptors are found in the adrenal medulla, as well as within the autonomic ganglia, that is on the cell surface of the postganglionic neuron at the synapse between the preganglionic and postganglionic neurons of both the sympathetic and parasympathetic systems. Nicotinic receptors are also found in many nonautonomic nerve endings, for example in the membranes of skeletal muscle fibers at the neuromuscular junction.

Acetylcholine is released from cholinergic neurons when small, clear, intracellular vesicles fuse with the presynaptic neuronal cell membrane. A wide variety of non-neuronal secretory cells, such as, adrenal medulla (as well as the PC12 cell line) and pancreatic islet cells release catecholamines and parathyroid hormone, respectively, from large dense-core vesicles. The PC12 cell line is a clone of rat pheochromocytoma cells extensively used as a tissue culture model for studies of sympathoadrenal development. Botulinum toxin inhibits the release of both types of compounds from both types of cells in vitro, permeabilized (as by electroporation) or by direct injection of the toxin into the denervated cell. Botulinum toxin is also known to block release of the neurotransmitter glutamate from cortical synaptosomes cell cultures.

A neuromuscular junction is formed in skeletal muscle by the proximity of axons to muscle cells. A signal transmitted through the nervous system results in an action potential at the terminal axon, with activation of ion channels and resulting release of the neurotransmitter acetylcholine from intraneuronal synaptic vesicles, for example at the motor endplate of the neuromuscular junction. The acetylcholine crosses the extracellular space to bind with acetylcholine receptor proteins on the surface of the muscle end plate. Once sufficient binding has occurred, an action potential of the muscle cell causes specific membrane ion channel changes, resulting in muscle cell contraction. The acetylcholine is then released from the muscle cells and metabolized by cholinesterases in the extracellular space. The metabolites are recycled back into the terminal axon for reprocessing into further acetylcholine.

As discussed above, the challenges of deploying the gastric band around the stomach and the risk of the band possibly slipping from its intended position may compromise the full potential use of the gastric band as a technique for affecting weight loss.

What is needed therefore is an improved method for facilitating weight loss.

SUMMARY

The present invention meets this need and provides for improved methods for facilitating the successful use of a gastric band leading weight loss in a patient. For example, the present invention allows the surgeon to maneuver the gastric band around the stomach more easily and/or to secure the band and prevent it from slipping off from the stomach.

In some embodiments, the methods comprise the steps of administering a neurotoxin to a stomach tissue of a patient, and deploying a gastric band around the stomach of the patient. The neurotoxin (e.g., botulinum toxin types A, B, $C_1$, D, E, F and G) may be locally administered or orally administered. In some embodiments, the neurotoxin is locally administered at or in a vicinity of the site where the gastric band contacts the stomach, for example, the upper part of the stomach.

In some embodiments, the neurotoxin is administered to a stomach tissue prior to the step of deploying a gastric band around the stomach. One of the advantages in pre-administering the stomach with a neurotoxin is that it relaxes the stomach and makes it more malleable. When the stomach is relaxed and is more malleable, it is easier for the surgeon to maneuver the band around the stomach, which would result in reduced operation time and faster recovery.

Another advantage of pre-administering the stomach tissue prior to deploying the gastric band around the stomach is that the stomach is relaxed and it is easier to adjust (e.g., tighten or loosen) the band around the stomach.

In some embodiments, the neurotoxin is administered at or in the vicinity of the site where the gastric band contacts the stomach. One of the advantages of locally administering a neurotoxin at a site or in the vicinity of the site where the gastric band contacts the stomach is that the band is better fitted at that site and would tend not to slip from that site. Without wishing to limit the invention to any theory or mechanism of operation, it is believed that the administration of the neurotoxin at or in the vicinity of the site where the band contacts the stomach creates a contrast region in muscle tone that would serve to secure the gastric band in place. For example, when the neurotoxin is administered at the site where the band contacts the stomach, the site administered has a relaxed muscle tone (see FIG. 2A). The gastric band would tend to “fall” into the region with the relaxed muscle tone—thus, the band would be secured in its intended site. In some embodiments, the gastric band is secured in that it does not twist around the stomach. In some embodiments, the gastric band is secured in that it does not slip off from the stomach.

Alternatively, the neurotoxin may be administered in the vicinity of the site where the band contacts the gastric band to create a contrast muscle tone region that would serve to secure the band in place. For example, a neurotoxin may be administered at a site above and/or below the site where the gastric band contacts the stomach (see FIG. 2B). This pattern of administration would create a contrast in muscle tone region such that the gastric band would tend to “fall” into the region that is not administered.

The term “neurotoxin” employed herein refers to one or more of a toxin made by a bacterium, for example, a *Clostridium botulinum, Clostridium butyricum, Clostridium beratti, Clostridium tetani*. In some embodiments, the neurotoxin is a botulinum toxin. The botulinum toxin may be a botulinum toxin type A, type B, type $C_1$, type D, type E, type F, or type G. In some embodiments, the neurotoxin is a botulinum toxin type A. Unless stated otherwise, the dose of the neurotoxin referenced herein is equivalent to that of a botulinum toxin type A. The assays required to determine equivalency to the therapeutic effectiveness of botulinum toxin type A at a certain dosage are well established.

Further, the botulinum toxin of the present invention may comprise a first element comprising a binding element able to specifically bind to a neuronal cell surface receptor under physiological conditions; a second element comprising a translocation element able to facilitate the transfer of a polypeptide across a neuronal cell membrane, and a third element comprising a therapeutic element able, when present in the cytoplasm of a neuron, to inhibit exocytosis of acetylcholine from the neuron. The therapeutic element can cleave a SNARE protein, thereby inhibiting the exocytosis of acetylcholine from the neuron. The SNARE protein can be selected from the group consisting of syntaxin, SNAP-25 and VAMP.

DEFINITIONS

The following definitions apply herein.

"About" means plus or minus ten percent of the value so qualified.

"Biocompatible" means that there is an insignificant inflammatory response upon ingestion of an oral formulation of a Clostridial toxin, as set forth herein.

"Effective amount" as applied to the biologically active compound means that amount of the compound which is generally sufficient to effect a desired change in the subject. For example, where the desired effect is decreasing the muscle tone of the stomach, an effective amount of the compound is that amount which causes at least a substantial decrease in the muscle tone of the stomach as determined by the pressure needed to be applied to tighten the gastric band around the stomach.

"Effective amount" as applied to a non-active ingredient constituent of an oral formulation (such as a polymer used for forming a matrix or a coating composition) refers to that amount of the non-active ingredient constituent which is sufficient to positively influence the release of a biologically active agent at a desired rate for a desired period of time. For example, where the desired effect is muscle paralysis by using a single oral formulation, the "effective amount" is the amount that can facilitate extending the release over a period of between about 60 days and 6 years. This "effective amount" can be determined based on the is teaching in this specification and the general knowledge in the art.

"Effective amount" as applied to the amount of surface area of an oral formulation is that amount of oral formulation surface area which is sufficient to effect a flux of biologically active compound so as to achieve a desired effect, such as a muscle paralysis or a decrease in the secretory activity of a gland. The area necessary may be determined and adjusted directly by measuring the release obtained for the particular active compound. The surface area of the oral formulation or of a coating of an oral formulation is that amount of membrane necessary to completely encapsulate the biologically active compound. The surface area depends on the geometry of the oral formulation. Preferably, the surface area is minimized where possible, to reduce the size of the oral formulation.

"Locally administering" or "local administration" means direct injection of a tissue, e.g., stomach tissue. For example, local administration to a stomach tissue may be accomplished by using an endoscope and a sclerotherapy needle (see U.S. Pat. No. 5,437,291, the disclosure of which is incorporated in its entirety herein by reference).

"Oral formulation" means a drug delivery system intended for oral ingestion. The oral formulation can be comprised of a biocompatible polymer or natural material which contains or which can act as a carrier for a molecule with a biological activity.

"Deploying" a gastric band around the stomach means wrapping the band around the stomach and positioning it at a desirable location, so that when tightened, the band pinches the stomach into an upper and a lower portion.

"Treatment" means any treatment of a disease (obesity) in a mammal, and includes: (i) preventing the disease from occurring or; (ii) inhibiting the disease, i.e., arresting its development; (iii) relieving the disease, i.e., reducing the incidence of symptoms of or causing regression of the disease.

DRAWINGS

DESCRIPTION

Figure 1A:
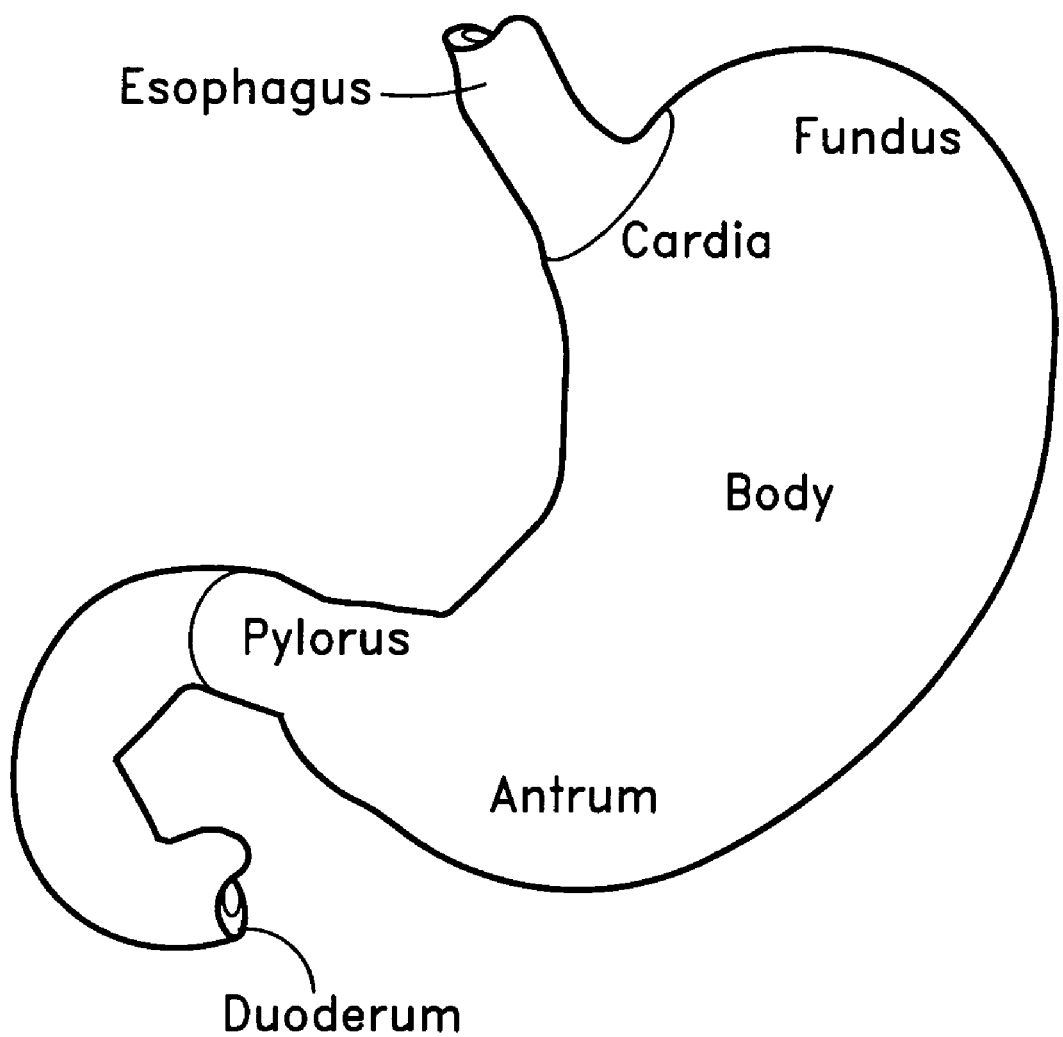
FIGS. 1A, 1B and 1C show the general diagram of the stomach; the longitudinal and circular muscular fibers of the stomach, viewed from above and in front; and the oblique muscular fibers of the stomach, viewed from above and in front, respectively.

The present invention is partly based upon the surprising discovery that an administration of a neurotoxin, such as a botulinum toxin, to a stomach tissue allows the gastric band to be more easily maneuvered around the stomach and subsequently adjusted (e.g., tightened or loosened). The present invention is also partly based on the surprising discovery that an administration of a neurotoxin at or in the vicinity of a site of the gastric band helps secure the band and prevents it from slipping off from the stomach.

In some embodiments, the methods comprise the steps of administering a neurotoxin to a stomach tissue of a patient, and deploying a gastric band around the stomach of the patient. In some embodiments, the stomach tissue is a smooth muscle of the stomach, e.g., longitudinal, circular and/or oblique. In some embodiments, the neurotoxin is administered to the circular muscle of the stomach.

The neurotoxin (e.g., botulinum toxin types A, B, $C_1$, D, E, F and G) may be locally administered. The neurotoxin may be locally administered using an endoscopic and/or laparoscopic procedure (see Example 2 below). In some embodiments, the neurotoxin is administered generally around the area where the gastric band is to be deployed. In some embodiments, the neurotoxin is administered to a stomach tissue prior to the step of deploying a gastric band around the stomach.

Various references have disclosed an endoscopic administration of botulinum toxin to a stomach to treat obesity. See, for example, Porta et al. (Mov Disord 2004, 19(9):S431

ABP1264); Albani et al. (J. Gastroenterol 2005, 40:833-835); Garcia-Compean et al. (Gastroenterol Clin Biol 2005, 29(8-9):789-791); U.S. Pat. App. Pub. 20040009224 to Miller; and U.S. Pat. App. Pub. 20040037865. These references disclose that the administration of a botulinum toxin to the stomach is effective to reduce motility of the stomach muscle (to slow down stomach emptying) and/or reduce the secretion of ghrelin, which presents a powerful signal of "hunger sensation" to the hypothalamus. However, the references do not teach or suggest that an administration of a neurotoxin, such as a neurotoxin, can be used in conjunction with a gastric band. More specifically, these references do not teach or suggest that an administration of a neurotoxin to a stomach tissue allows the gastric band to be more easily maneuvered around the stomach and subsequently adjusted (e.g., tightened or loosened), or that an administration of a neurotoxin at or in the vicinity of a site of the gastric band helps secure the band and prevents it from slipping off from the stomach.

In some embodiments, the neurotoxin is orally administered. The neurotoxin may be administered to the stomach via an oral ingestion of a neurotoxin oral formulation. For example, a neurotoxin oral formulation within the scope of the present invention is capable of releasing a effective amount of a neurotoxin into the stomach of a patient to relax the stomach muscle. The amount of released neurotoxin can comprise as little as about 10 units (based on the units of botulinum toxin type A) (i.e. to relax the stomach muscle of a patient weighing less than 50 kg) to as much as 500 units (i.e. to relax the stomach muscle of a large adult). The quantity of botulinum toxin required to effectively relax a stomach muscle can be varied according to the known clinical potency of the different neurotoxins, e.g., botulinum toxin serotypes. For example, several orders of magnitude more units of a botulinum toxin type B are typically required to achieve a physiological effect comparable to that achieved from use of a botulinum toxin type A.

The specific dosage by oral formulation appropriate for administration is readily determined by one of ordinary skill in the art according to the factors discussed above. The dosage can also depend upon the size of the tissue mass to be treated or denervated, and the commercial preparation of the toxin. Additionally, the estimates for appropriate dosages in humans can be extrapolated from determinations of the amounts of botulinum required for effective denervation of other tissues. Thus, the amount of botulinum A to be injected is proportional to the mass and level of activity of the tissue to be treated. Generally, between about 0.01 units per kilogram to about 35 units per kg of patient weight of a botulinum toxin, such as botulinum toxin type A, can be released by the present oral formulation per unit time period (i.e. over a period of or once every 2-4 months) to effectively accomplish a desired relaxation of the stomach muscle. Less than about 0.01 U/kg of a botulinum toxin may not have a significant therapeutic effect upon a stomach endocrine cell, while more than about 35 U/kg of a botulinum toxin approaches a toxic dose of a Clostridial toxin, such as a botulinum toxin type A. Careful preparation of the oral formulation prevents significant amounts of a botulinum toxin from appearing systemically. A more preferred dose range is from about 0.01 U/kg to about 25 U/kg of a botulinum toxin, such as that formulated as BOTOX®. The actual amount of U/kg of a botulinum toxin to be administered depends upon factors such as the extent (mass) and level of activity of the tissue to be treated and the administration route chosen. Botulinum toxin type A is a preferred botulinum toxin serotype for use in the methods of the present invention.

The oral formulation may be prepared so that the neurotoxin is substantially uniformly dispersed in a biodegradable carrier. An alternate oral formulation within the scope of the present invention can comprise a carrier coated by a biodegradable coating, either the thickness of the coating or the coating material being varied.

The thickness of the oral formulation can be used to control the absorption of water by, and thus the rate of release of a neurotoxin from, a composition of the invention, thicker oral formulations releasing the polypeptide neurotoxin more slowly than thinner ones.

The neurotoxin in a neurotoxin controlled release composition can also be mixed with other excipients, such as bulking agents or additional stabilizing agents, such as buffers to stabilize the neurotoxin during lyophilization. Additional details regarding a neurotoxin formulation suitable for oral delivery may be found in, for example, U.S. Ser. No. 10/288,906 and Ser. No. 10/459,767 (Attorney Docket Nos. 17539 and 17586, respectively), the disclosures of which are incorporated in their entirety herein by reference.

In some embodiments, the neurotoxin is administered to the stomach prior to deploying the gastric band around the stomach. One of the advantages in pre-administering the stomach with a neurotoxin is that it relaxes the stomach and makes it more malleable. When the stomach is relaxed and is more malleable, it is easier for the surgeon to maneuver the band around the stomach, which would result in reduced operation time and faster recovery. For example, a standard gastric band procedure takes about 30-45 minutes. With a pre-administration of a neurotoxin, the procedure may be faster by about 10-40%, as the surgeon is better able to maneuver around a more malleable stomach. Also, a pre-administration of a neurotoxin results in a faster healing time. For example, after a conventional gastric band procedure, most patients are able to return to normal functions after about 5-7 days. However, an administration of a neurotoxin prior to a gastric band procedure would result in patients being able to return to normal functions about 10-40% faster, as compared to patients undergoing the same procedure but without the pre-administration of a neurotoxin.

Another advantage of administering the neurotoxin to a stomach tissue prior to deploying the gastric band around the stomach is that the stomach is relaxed and it is easier to adjust (e.g., tighten or loosen) the band around the stomach. For example, after the gastric band is deployed around the stomach, the patient is scheduled for a regular check up. During this check up, the band may be adjusted (tightened or loosened) to decrease or increase the size of the stoma. This is a quick and relatively painless outpatient procedure. Usually, the patient is x-rayed during the procedure so that the band reservoir or "port" can be seen clearly. Then, a fine needle is passed through the skin into the port to add or remove saline. Adding saline tightens the band, further restricting the amount of food the patient can eat before feeling full and satisfied. When the stomach is administered with a neurotoxin, stomach area forming the stoma is more malleable, allowing for more accurate adjustment and calibration of the stoma size, and thus, better facilitation of weight loss.

My invention also includes a method for facilitating weight loss by deploying a gastric band around the stomach of the patient wherein the gastric band has previously been coated, on the side of the gastric band which will be in contact with stomach tissue, with a botulinum toxin, such as a botulinum toxin type A. Thus upon positioning of the gastric band in contact with the stomach, the botulinum toxin is absorbed into or diffuses into the adjacent stomach tissue. Technologies for coating a medical device with a botulinum toxin are known. See e.g. U.S. Pat. Nos. 6,767,544 and 6,579,847.

Figure 1B:
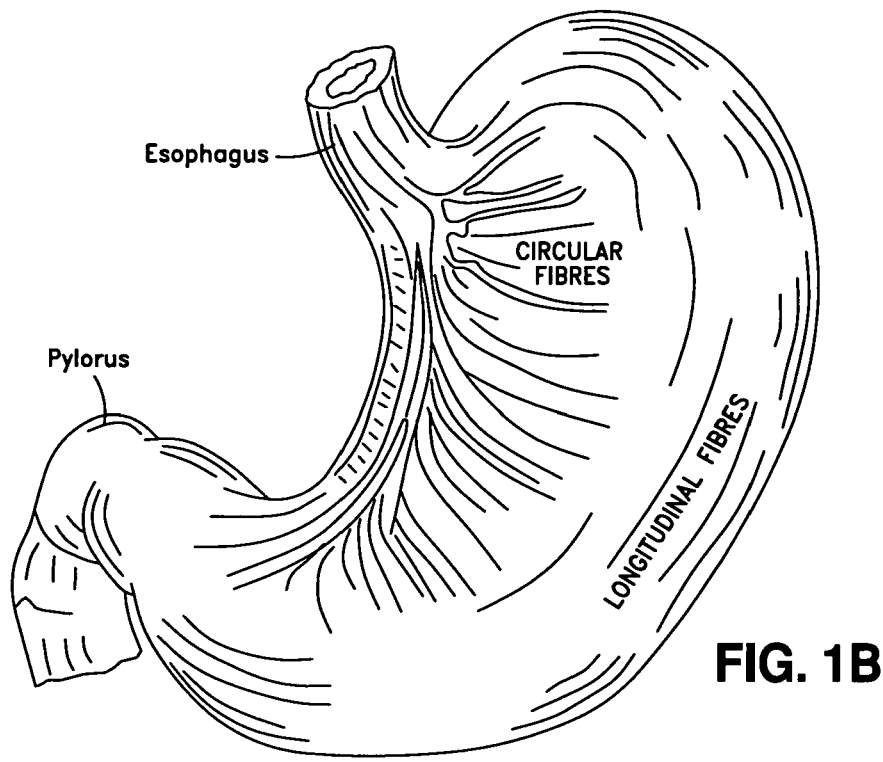
Figure 1C:
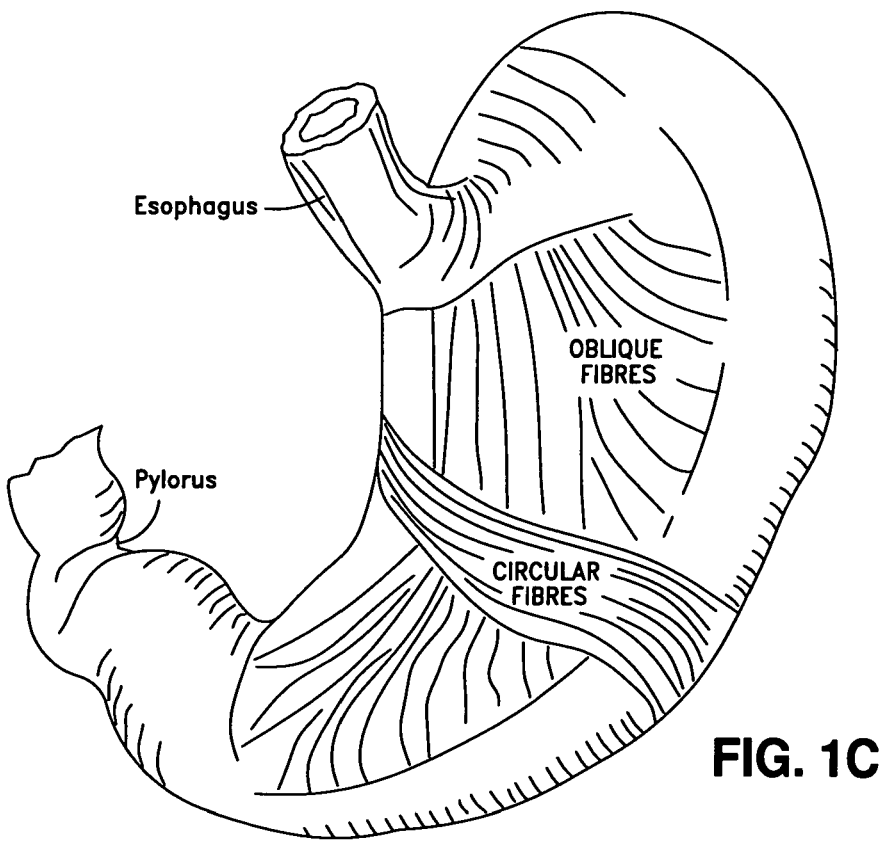
Figure 2A:
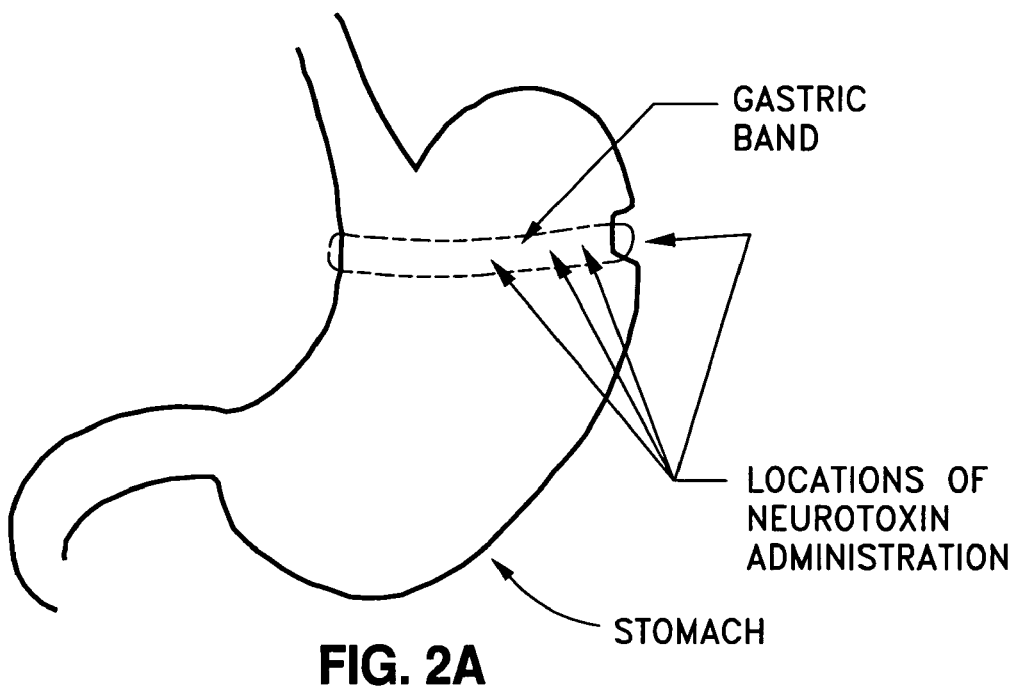
FIGS. 2A and 2B show examples of an administration of a neurotoxin at a site where the gastric band contacts the stomach, and in the vicinity of the site where the gastric band contacts the stomach.

In some embodiments, the neurotoxin is administered at or in the vicinity of the site where the gastric band contacts the stomach. One of the advantages of locally administering a neurotoxin at a site or in the vicinity of the site where the gastric band contacts the stomach is that the band is better fitted at that site and would tend not to slip from that site. Without wishing to limit the invention to any theory or mechanism of operation, it is believed that the administration of the neurotoxin at or in the vicinity of the site where the band contacts the stomach creates a contrast in muscle tone region that would serve to secure the gastric band in place. For example, when the neurotoxin is administered at the site where the band contacts the stomach, the site administered has a relaxed muscle tone (see FIG. 2A). The gastric band would tend to "fall" into the region with the relaxed muscle tone—thus, the band would be secured in its intended location. One or more sites on the stomach may be administered. In some embodiments, the neurotoxin is administered along the entire circumference of the stomach. In some embodiments, the neurotoxin is administered substantially on the greater curvature side of the stomach (FIG. 1 and FIG. 2A). In some embodiments, the neurotoxin is administered on the stomach at sites that are about 1-10 cm apart. In some embodiments, about 0.5-10 units based on botulinum toxin type A) of a neurotoxin is administered to each site.

Figure 2B:
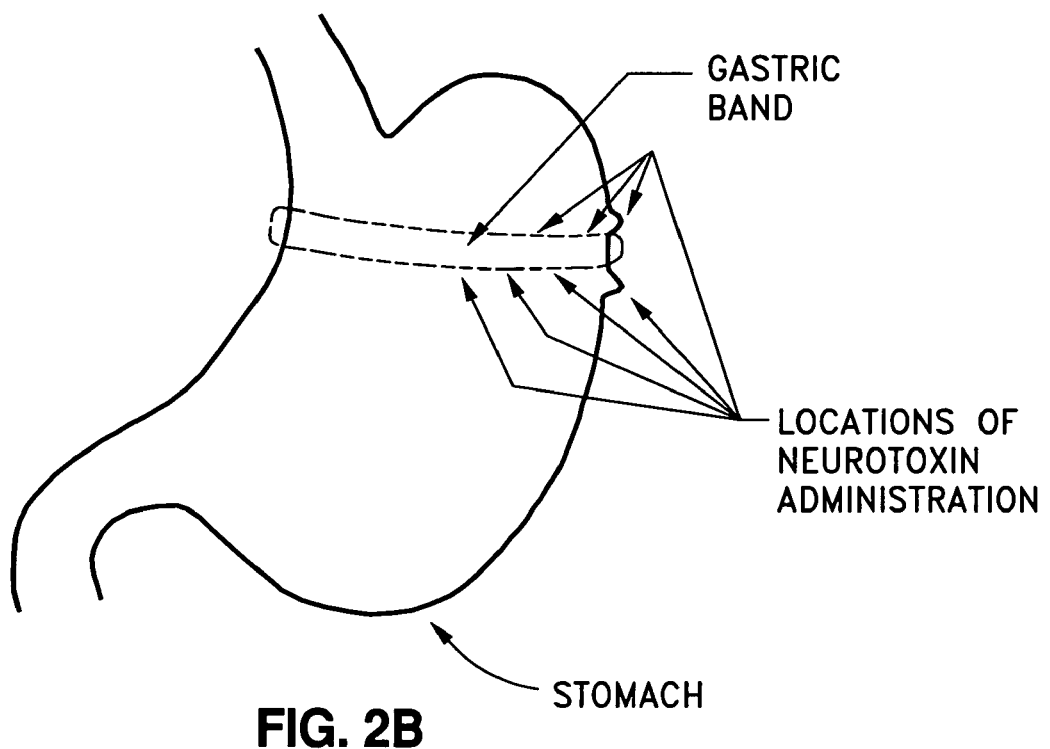
Figure 3:
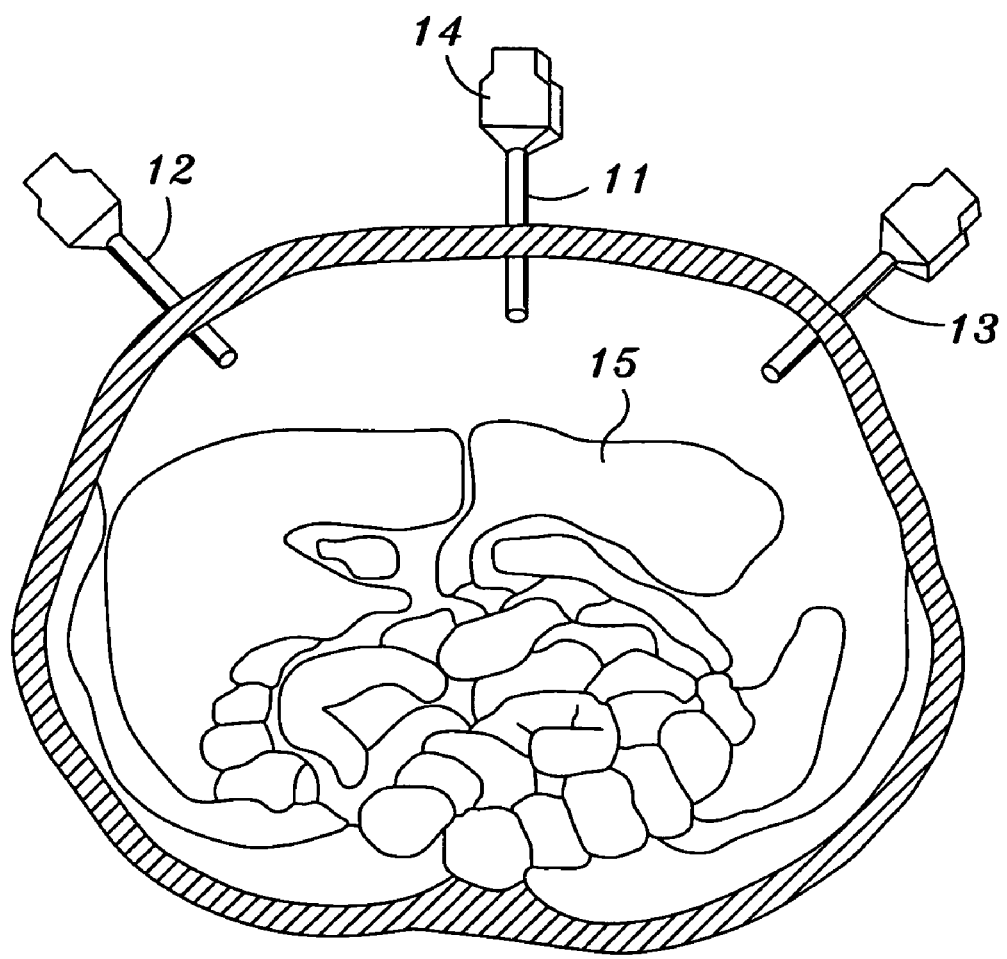
FIG. 3 shows a cross-sectional view of the torso of a patient showing the placement of trocars for the introduction of a laparoscopic gastric band.

Alternatively, the neurotoxin may be administered in the vicinity of the site where the band contacts the gastric band to create a contrast muscle tone region that would serve to secure the band in place. For example, a neurotoxin may be administered at a site above and/or below the site where the gastric band contacts the stomach (see FIG. 2B). This pattern of administration would create a contrast in muscle tone such that the gastric band would tend to "fall" into the region that is not administered. In some embodiments, the neurotoxin is administered along the entire circumference of the stomach. In some embodiments, the neurotoxin is administered substantially on the greater curvature side of the stomach (FIG. 1 and FIG. 2B). In some embodiments, the neurotoxin is administered on the stomach at sites that are about 1-10 cm apart. In some embodiments, about 0.5-10 units based on botulinum toxin type A) of a neurotoxin is administered to each site.

Preferably, a neurotoxin used to practice a method within the scope of the present invention is a botulinum toxin, such as one of the serotype A, B, C, D, E, F or G botulinum toxins. Preferably, the botulinum toxin used is botulinum toxin type A, because of its high potency in humans, ready availability, and known safe and efficacious use for the treatment of skeletal muscle and smooth muscle disorders when locally administered by intramuscular injection.

The present invention includes within its scope: (a) Clostridial toxin complex as well as pure Clostridial toxin obtained or processed by bacterial culturing, toxin extraction, concentration, preservation, freeze drying and/or reconstitution and; (b) modified or recombinant Clostridial toxin, that is Clostridial toxin that has had one or more amino acids or amino acid sequences deliberately deleted, modified or redeployed by known chemical/biochemical amino acid modification procedures or by use of known host cell/recombinant vector recombinant technologies, as well as derivatives or fragments of Clostridial toxins so made, and includes Clostridial toxins with one or more attached targeting moieties for a cell surface receptor present on a cell.

Neurotoxins, e.g., botulinum toxins, for use according to the present invention can be stored in lyophilized or vacuum dried form in containers under vacuum pressure. Prior to lyophilization the botulinum toxin can be combined with pharmaceutically acceptable excipients, stabilizers and/or carriers, such as albumin. The lyophilized or vacuum dried material can be reconstituted with saline or water.

Methods for determining the appropriate route of administration and dosage are generally determined on a case by case basis by the attending physician. Such determinations are routine to one of ordinary skill in the art (see for example, *Harrison's Principles of Internal Medicine* (1998), edited by Anthony Fauci et al., $14^{th}$ edition, published by McGraw Hill).

EXAMPLES

The following examples set forth specific compositions and methods encompassed by the present invention and are not intended to limit the scope of the present invention.

Example 1

Laparoscopic Procedure for Deploying a Gastric Band

In the discussion that follows, reference is made to FIGS. 3-8. For clarity, the trocar cannulas have been omitted from these figures. It should be understood, however, that all intra-abdominal instruments or exogenous assemblies referred to in the figures pass through a laparoscopic cannula.

The surgical technique is as follows:

Step 1. Routine procedures for laparoscopic surgical entrance into the abdominal cavity are followed. Typically, a semicircular incision about 20 mm in length is made at the lower edge of the umbilicus. A trocar 11 (FIG. 3) is inserted through an incision into the peritoneal cavity. The laparoscope 14 is inserted through the sleeve of the trocar 11 and the abdomen insufflated to a pressure of 14-16 mm of mercury. The pressure should never exceed 20 mm of mercury. With abdominal distension, the intraperitoneal viscera are visible. At this time, a video camera (not shown) may be connected to the laparoscope 14. Once the abdomen is properly insufflated, trocars 12 and 13 are inserted under the following guidelines: a) each entrance port is inspected to assure it is a safe area; and b) each insertion is observed through the laparoscope from within to assure no viscera is injured. More additional cannulas may be inserted as the need arises. Once the upper stomach is exposed, adhesions, if present, are transected. The stomach is pulled down (caudal) and the gastrophrenic ligament is opened proximal to the short gastric vessels.

Step 2. Mid-line (2-3") long skin incision in midway between the xyphoid process and the umbilicus. The incision is carried out through the subcutaneous fat to the linea alba. The right rectus sheath is exposed but no space for implantation of the injection port is prepared at this time.

Figure 4:
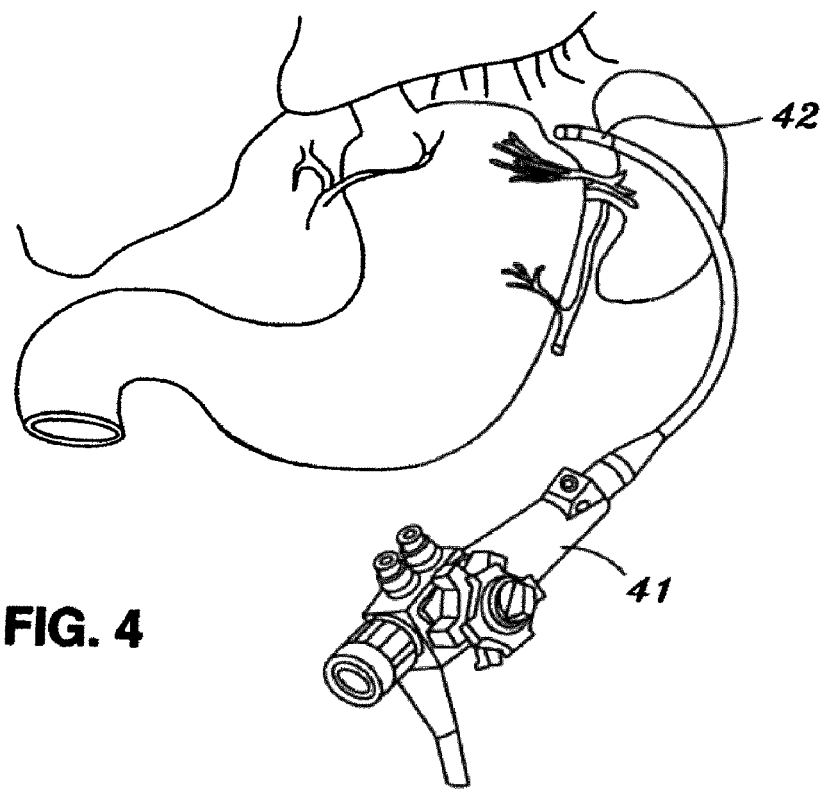
FIG. 4 shows the insertion of a modified flexible endoscope into the upper abdomen.
Figure 5:
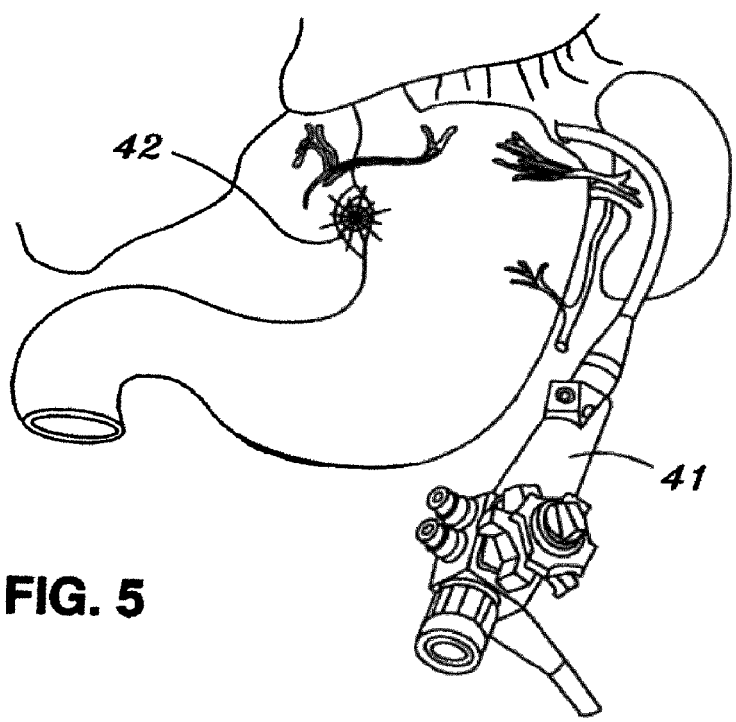
FIG. 5 shows a perspective view of the flexible endoscope with a light on the tip to facilitate dissection along the lesser curvature of the stomach.
Figure 6:
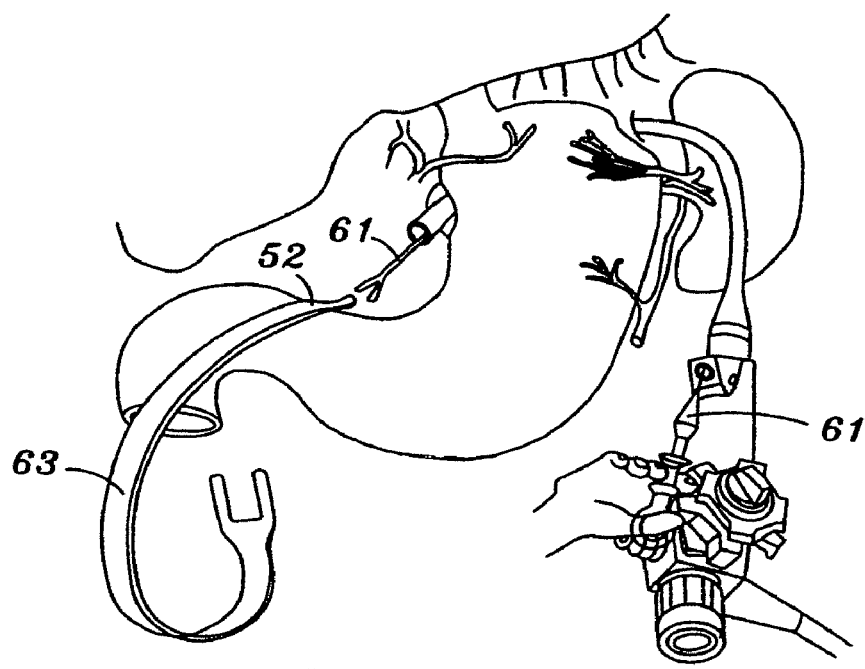
FIG. 6 shows forceps inserted through the lumen of the endoscope prior to grasping the tail end of a gastric band.

Step 3. As shown in FIG. 4, a modified flexible endoscope 41 is inserted into the abdominal cavity. Using the flexible part 42 of the endoscope 41, blunt dissection is made at the greater curvature. A tunnel is dissected under the stomach toward the lesser curvature as shown by the position of the flexible end 42 of the endoscope 41 in FIG. 5. The optical system of the scope is useful during the dissection. In particular, at the lesser curvature, the light on the scope will make dissection easier and safer (FIG. 5).

Step 4. When the opening next to the lesser curvature is made, forceps 61 (FIG. 6) are inserted through the channel in the endoscope 41. The tail end of the gastric band 62 is grasped with the forceps 61 (FIG. 6); and, when withdrawing the endoscope 41, the band is threaded under the stomach. The head and tail ends of the gastric band are brought together.

Figure 7:
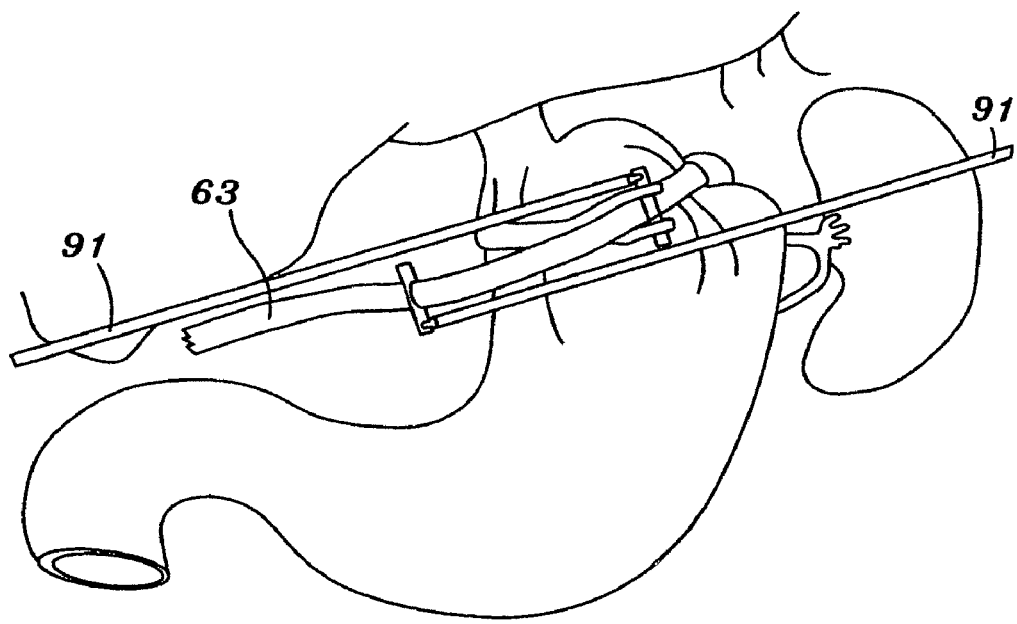
FIG. 7 is a perspective view of the gastric band being held for adjustment of the stoma size during the calibration procedure.

Step 5. A pair of banding instruments 91 are inserted into the abdominal cavity. The head and tail ends of the gastric band are brought together into adjustable alignment and clamped with the respective jaws of the banding instrument 91 as shown in FIG. 7. The balloon (not shown) on the band is pre-inflated with saline solution.

Step 6. The calibration tube (not shown) is then inserted into the stomach by the anesthesiologist through the mouth and the band is tightened by hand until it is firmly in place over the calibration tube in the manner well known in the prior art. The greater curvature is sutured over the band to the pouch. Using the banding instruments the band is carefully tightened until the correct stoma diameter is obtained.

Step 7. The band holder or any other modified attachment device is then applied. The banding instruments and calibration tube are removed.

Step 8. The overlapping ends of the band are sutured together in the calibrated position (or clipped with clips).

Figure 8:
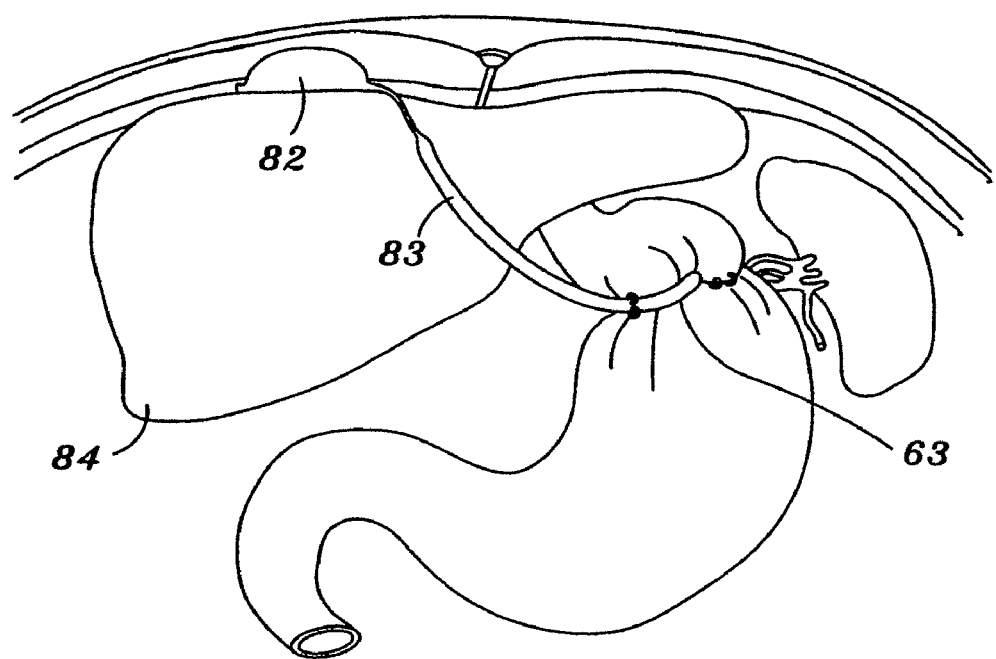
FIG. 8 shows the gastric band in position around the stomach with an injection port passing underneath the liver and threaded into the space within the rectus sheath for implantation.

Step 9. As shown in FIG. 8, subcutaneous fat overlying the right rectus sheath is dissected for access to the rectus sheaths for implantation of the injection port.

Step 10. The fill tube 83 is deployed under the liver 84 to create the shortest path between the band 63 and the injection site 82 and threaded into the previously dissected receiving space within the rectus sheath. The fill tube 83 is connected to the injection port 82. The incisions are closed in the usual fashion.

It is clear that the foregoing procedure may be modified and be useful for deploying any gastric band (including the LAP-BAND® SYSTEM) into an encircling position around the stomach.

Example 2

Injection of Botulinum Toxin Using Endoscopic Techniques

To locally administer a neurotoxin to a stomach site, an endoscopy is performed with a standard adult forward-viewing instrument. The site of administration on the stomach is estimated both endoscopically as well as by a previously performed manometry. At the administration site, a neurotoxin, e.g., botulinum toxin type A is injected via a 4-mm sclerotherapy needle passed thorough the biopsy channel of the endoscope. One milliliter of a 10 U/mL solution can be injected into each site on the stomach (see U.S. Pat. No. 5,437,291, the disclosure of which is incorporated in its entirety herein by reference).

Example 3

Method for Facilitating Weight Loss (With Local Administration of Botulinum Toxin to the Stomach)

A male patient being at least 60-100 pounds overweight. The patient is a good candidate for a gastric band procedure to help him loose weight.

The patient wishes to loose weight and elects to undergo a LAP-BAND® procedure. A few weeks prior to and/or at the time of the actual LAP-BAND® procedure, the patient is administered with a botulinum toxin to relax the stomach muscles. Using endoscopic techniques, the botulinum toxin is administered to the upper part of the stomach, preferably to or in the vicinity of a site where the band is to be deployed ("in the vicinity" of the site means, for example, within about less than 10 cm from the site of where the band is to be deployed on the stomach).

The time gap between the pre-administration of the botulinum toxin and LAP-BAND® procedure depends on the dose and botulinum toxin type administered. Preferably, the muscle tone of the stomach muscle is relaxed by at least more than about 50% of the maximum contraction prior to performing LAP-BAND® procedure.

When the patient is ready for the LAP-BAND® procedure, the patient is placed on a no fat, liquid diet for 7 days before the surgery. The purpose of this liquid diet is to decrease the size of the liver, which in turn will make the placement of the LAP-BAND® safer.

The LAP-BAND® procedure performed after the stomach is relaxed by the administration of a botulinum toxin takes less time as compared to the same procedure where the stomach is not relaxed by the administration of a botulinum toxin, as the surgeon can maneuver around the stomach more easily. In this case, the LAP-BAND® procedure is around 25 minutes, which is about 10 minutes faster than usual. Moreover, the recovery time (time the patient is able to resume normal daily functions) from the LAP-BAND® procedure performed after the stomach is relaxed by the administration of a botulinum toxin is faster as compared to that of the same procedure where the stomach is not relaxed by the administration of a botulinum toxin. In this case, the recovery time is about 4 days, which is about 1 or 2 days faster than usual.

Example 4

Method for Facilitating Weight Loss (with Oral Botulinum Toxin Formulation)

A middle age female patient with a BMI (Body Mass Index) of between 30-60. The patient is a good candidate for a gastric band procedure to help her loose weight.

The patient wishes to loose weight and elects to undergo a LAP-BAND® procedure. A few weeks prior and/or at the time of the LAP-BAND® procedure, the patient is administered with an oral botulinum toxin formulation to relax the stomach muscles.

The time gap between the pre-administration of the botulinum toxin and LAP-BAND® procedure depends on the dose and botulinum toxin type administered. Preferably, the muscle tone of the stomach muscle is relaxed to at least more than about 75% of the maximum contraction prior to performing LAP-BAND® procedure.

The LAP-BAND® procedure is performed after the surgeon determines that the stomach is adequately relaxed by the administration of a botulinum toxin. The LAP-BAND® procedure takes less time as compared to the same procedure where the stomach is not relaxed by the administration of a botulinum toxin, as the surgeon can maneuver around the stomach more easily. In this case, the LAP-BAND® procedure is around 25 minutes, which is about 5 minutes faster than usual. Moreover, the recovery time from the LAP-BAND® procedure performed after the stomach is relaxed by the administration of a botulinum toxin is faster as compared to that of the same procedure where the stomach is not relaxed by the administration of a botulinum toxin. In this case, the recovery time is about 3 days, which is about 2-3 days faster than usual.

Example 5

Method for Making a Botulinum Toxin Tablet for Oral Ingestion

A botulinum toxin can be compounded as an oral formulation for release of the toxin active ingredient into the stomach or duodenum. This is easily accomplished by mixing with a mortar and pestle (at room temperature without addition of any water or saline) 50 units of a commercially available lyophilized botulinum toxin powder, such as non-reconstituted BOTOX® (or 200 units of DYSPORT® powder) with a biodegradable carrier such as flour or sugar. Alternately, the botulinum toxin can be mixed by homogenization or sonication to form a fine dispersion of the powdered toxin in the carrier. The mixture can then compressed with a tablet making machine (such as the tablet press available from Scheu & Kniss, 1500 W. Ormsby Ave, Louisville, Ky. 40210) to make an ingestible tablet. Alternately, the toxin can be formulated with gelatin by well known methodologies to make an ingestible geltab.

Example 6

Method For Securing a Gastric Band In Place

One of the complications of a gastric band procedure is that after the gastric band procedure is completed, the gastric band can slip out of position, which may cause obstruction of the stomach. To prevent the band from slipping out of position, the surgeon locally administers botulinum toxin along the circumference line of where the gastric band is to contact the stomach. In this case, the botulinum toxin is administered at five sites (each site being about 2 cm apart) to the greater curvature side of the stomach along the circumference line of where the gastric band is to contact the stomach (FIG. 2A). The administration of the botulinum toxin causes a contrast in muscle tone between the administered and non-administered region.

Subsequent to the local administration of botulinum toxin, the surgeon deploys the gastric band around the stomach. The band snuggly falls into the region on the stomach that has been administered with a botulinum toxin. Thus, the stomach effectively "traps" the band, and prevents it from slipping off. The band remains in place on the stomach for more than one year.

Methods according to the invention disclosed herein has many advantages, including the following:

All references, articles, publications and patents and patent applications cited herein are incorporated by reference in their entireties.

Although the present invention has been described in detail with regard to certain preferred methods, other embodiments, versions, and modifications within the scope of the present invention are possible. For example, a wide variety of Clostridial toxins can be effectively used in the methods of the present invention. Additionally, the present invention includes oral formulations where two or more botulinum toxins, are administered concurrently or consecutively via the oral formulation. For example, botulinum toxin type A can be administered via an oral formulation until a loss of clinical response or neutralizing antibodies develop, followed by administration also by suitable oral formulation of a botulinum toxin type B or E. Alternately, a combination of any two or more of the botulinum serotypes A-G can be locally administered to control the onset and duration of the desired therapeutic result. Furthermore, non-Clostridial toxin compounds can be administered prior to, concurrently with or subsequent to administration of the Clostridial toxin via oral formulation so as to provide an adjunct effect such as enhanced or a more rapid onset of denervation before the Clostridial toxin, such as a botulinum toxin, begins to exert its therapeutic effect.

Accordingly, the spirit and scope of the following claims should not be limited to the descriptions of the preferred embodiments set forth above.

What is claimed is:

1. A method for facilitating weight loss, the method comprising the steps of: (a) administering a botulinum toxin to a stomach tissue of a patient; and (b) deploying a gastric band around the stomach of the patient and within about less than 10 cm from the stomach tissue to which the botulinum toxin is administered to provide a contrast muscle tone region on the stomach, thereby facilitating weight loss by the patient.

2. The method of claim 1, wherein the step of administering is administering locally.

3. The method of claim 2, wherein the botulinum toxin is administered locally at a site or in a vicinity of the site where the gastric band contacts the stomach.

4. The method of claim 2, wherein the botulinum toxin is administered locally to an upper part of the stomach.

5. The method of claim 1, wherein the step of administering the botulinum toxin relaxes a muscle of the stomach prior to the step of deploying the gastric band around the stomach.

6. The method of claim 1, further comprising the step of: (c) tightening or loosening the gastric band around the stomach.

7. The method of claim 6, wherein the step of administering the botulinum toxin relaxes a muscle of the stomach prior to the step of tightening or loosening of the gastric band.

8. The method of claim 1, wherein the botulinum toxin is a botulinum toxin selected from the group consisting of botulinum toxins types A, B, $C_1$, D, E, F and G.

9. The method of claim 1, wherein the botulinum toxin is a botulinum toxin type A.

10. The method of claim 1, wherein the patient is an obese patient.

11. The method of claim 1, wherein the stomach tissue is a stomach smooth muscle.

12. A method for treating obesity, the method comprising the steps of: (a) administering a botulinum toxin type A to a muscle of a stomach of an obese patient to provide a contrast muscle tone region on the stomach; and (b) deploying a gastric band around the stomach of the obese patient and within about less than 10 cm from where the botulinum toxin is administered to provide the contrast muscle tone region on the stomach, thereby treating the obesity.

13. The method of claim 12, further comprising the step of: (c) tightening or loosening the gastric band around the stomach in conjunction with a prior injection of botulinum toxin locally to the muscle.

14. A method for securing a gastric band in place around a stomach, the method comprising the steps of: (a) locally administering a botulinum toxin to a stomach at a site or in a vicinity of a site where the gastric band contacts the stomach, wherein the administration of the botulinum toxin creates a contrast muscle tone region on the stomach and wherein the botulinum toxin is administered along a line where the gastric band is to contact the stomach; (b) deploying the gastric band around the stomach, wherein the gastric band fits into the contrast muscle tone region, thereby securing the gastric band to the stomach.

15. The method of claim 14, wherein the site of botulinum toxin administration is on a greater curvature side of the stomach.

16. The method of claim 14, wherein the step of locally administering the botulinum toxin is to more than one site on the stomach.

17. The method of claim 14, wherein the botulinum toxin is a botulinum toxin selected from the group consisting of botulinum toxins types A, B, $C_1$, D, E, F and G.

18. The method of claim 14, wherein the botulinum toxin is a botulinum toxin type A.

19. The method of claim 14, wherein the gastric band is secured to the stomach by not slipping off from the stomach.

20. A method for deploying a gastric band around a stomach, the method comprising the steps of: (a) administering a botulinum toxin circumferentially to a stomach tissue of a patient to provide a contrast muscle tone region on the stomach; and (b) deploying a gastric band around the stomach of the patient; wherein the gastric band is deployed within about less than 10 cm from the stomach tissue to which the botulinum toxin is administered.

21. The method of claim 20, wherein the botulinum toxin is administered locally.

22. The method of claim 20, wherein the botulinum toxin is administered locally at a site or in a vicinity of the site where the gastric band contacts the stomach.

23. The method of claim 20, wherein the botulinum toxin is administered locally to an upper part of the stomach.

24. The method of claim 20, wherein the step of administering the botulinum toxin relaxes a muscle of the stomach prior to the step of deploying the gastric band around the stomach.

25. The method of claim 20, further comprising the step of: (c) tightening or loosening the gastric band around the stomach.

26. The method of claim 25, where the step of administering the botulinum toxin relaxes a muscle of the stomach prior to the step of tightening or loosening of the gastric band.

27. The method of claim 20, wherein the botulinum toxin is a botulinum toxin selected from the group consisting of botulinum toxins types A, B, $C_1$, D, E, F and G.

28. The method of claim 20, wherein the botulinum toxin is a botulinum toxin type A.

29. The method of claim 20, wherein the patient is an obese patient.

30. The method of claim 20, wherein the stomach tissue is a stomach smooth muscle.

31. A method for facilitating weight loss, the method comprising the steps of: (a) coating a botulinum toxin onto a surface of a gastric band intended to contact a stomach of a patient; and (b) deploying the gastric band having the botulinum toxin coated thereon around the stomach of the patient to provide a contrast muscle tone region on the stomach associated with the gastric band coated with the botulinum toxin, thereby facilitating weight loss by the patient.

32. The method of claim 31, wherein the botulinum toxin is a botulinum toxin selected from the group consisting of botulinum toxins types A, B, $C_1$, D, E, F and G.

33. The method of claim 31, wherein the botulinum toxin is a botulinum toxin type A.

\* \* \* \* \*

UNITED STATES PATENT AND TRADEMARK OFFICE
CERTIFICATE OF CORRECTION

| | | |
|---|---|---|
| PATENT NO. | : 7,794,386 B2 | |
| APPLICATION NO. | : 11/376667 | |
| DATED | : September 14, 2010 | |
| INVENTOR(S) | : Gregory F. Brooks | |

It is certified that error appears in the above-identified patent and that said Letters Patent is hereby corrected as shown below:

On page 2, in column 2, under "Other Pubications", line 60, delete Nauny-Schmiedeberg's" and insert -- Naunyn-Schmiedeberg's --, therefor.

In column 3, line 12, delete "(fibræobliquæ)" and insert -- (fibræ obliquæ) --, therefor.

In column 5, line 35, delete "hemaglutinin" and insert -- hemagglutinin --, therefor.

In column 5, line 36, delete "nonhemaglutinin" and insert -- nonhemagglutinin --, therefor.

In column 9, line 43, delete "sublimes:" and insert -- sublimis: --, therefor.

In column 10, line 8, delete "rhinittis," and insert -- rhinitis, --, therefor.

In column 10, line 24, delete "hyperhydrosis" and insert -- hyperhidrosis --, therefor.

In column 10, lines 34-35, delete "Nauny-Schmiedeberg's" and insert -- Naunyn-Schmiedeberg's --, therefor.

In column 10, line 38, delete "Nauny-Schmiedeberg's" and insert -- Naunyn-Schmiedeberg's --, therefor.

In column 10, line 59, delete "hyperhydrosis" and insert -- hyperhidrosis --, therefor.

In column 11, line 49, delete "know" and insert -- known --, therefor.

In column 12, line 23, delete "gangliocide" and insert -- ganglioside --, therefor.

In column 15, line 39, before "teaching" delete "is".

Signed and Sealed this
Twelfth Day of April, 2011

David J. Kappos
*Director of the United States Patent and Trademark Office*

CERTIFICATE OF CORRECTION (continued)
U.S. Pat. No. 7,794,386 B2

In column 21, line 47, delete "thorough" and insert -- through --, therefor.

In column 23, line 18, delete "Ky." and insert -- KY --, therefor.